(12) United States Patent
Lee et al.

(10) Patent No.: US 12,221,611 B2
(45) Date of Patent: Feb. 11, 2025

(54) ASTROCYTE-SPECIFIC NUCLEIC ACID APTAMER AND USE THEREOF

(71) Applicant: IUCF-HYU (INDUSTRY-UNIVERSITY COOPERATION FOUNDATION HANYANG UNIVERSITY), Seoul (KR)

(72) Inventors: Eun-Song Lee, Seongnam-si (KR); Miso Kim, Gyeongju-si (KR); Jin Saem Lee, Seoul (KR); Chang-Hwan Park, Seoul (KR); Young-Pil Kim, Seoul (KR); Eun Hye Lee, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 852 days.

(21) Appl. No.: 17/285,351

(22) PCT Filed: Oct. 15, 2019

(86) PCT No.: PCT/KR2019/013539
§ 371 (c)(1),
(2) Date: May 11, 2021

(87) PCT Pub. No.: WO2020/080809
PCT Pub. Date: Apr. 23, 2020

(65) Prior Publication Data
US 2021/0371864 A1    Dec. 2, 2021

(30) Foreign Application Priority Data

Oct. 15, 2018    (KR) ........................ 10-2018-0122835

(51) Int. Cl.
| | | |
|---|---|---|
| *A61K 38/16* | (2006.01) | |
| *C12N 15/115* | (2010.01) | |
| *G01N 33/531* | (2006.01) | |
| *G01N 33/569* | (2006.01) | |

(52) U.S. Cl.
CPC ..... *C12N 15/115* (2013.01); *G01N 33/56966* (2013.01); *C12N 2310/16* (2013.01); *C12N 2320/13* (2013.01)

(58) Field of Classification Search
None
See application file for complete search history.

(56) References Cited

U.S. PATENT DOCUMENTS

2018/0044663 A1    2/2018    Yan

FOREIGN PATENT DOCUMENTS

| CN | 107462714 A | 12/2017 |
|---|---|---|
| KR | 10-2008-0105597 A | 12/2008 |
| KR | 10-2017-0013178 A | 2/2017 |

OTHER PUBLICATIONS

Jeong, Gijun, "Recent Trend on Development and Usage of Aptamer", Intelligent biodesigneering a Powerful Tool for Revolution in Biotechnology, Mar. 22, 2017, pp. 1-10, URL: http://www.syntheticbiology.or.kr/board.php?db=sub0302&uid=2&no=208& e=view&page=1 &sch_sell=&sch_sei2=&sch_sel3=&sch_value=.
Flora Vasile et al., "Human astrocytes: structure and functions in the health brain", Brain structure & function, 2017, pp. Feb. 17, 2029, vol. 222.
Hijiri Hasegawa, "Methods for Improving Aptamer Binding Affinity", Molecules, 2016, pp. 1-15, vol. 21, Document 421.
Michael Zuker, "Mfold web server for nucleic acid folding and hybridization prediction", Nucleic Acids Resaech,2003, pp. 3406-3415, vol. 31, No. 13.
Takeshi Tokunaga et al., "Cell Surface-Anchored Fluorescent Aptamer Sensor Enables Imaging of Chemical Transmitter Dynamics", J. Am. Chem. Soc., 2012, pp. 9561-9564, vol. 134.
Office Action for Korean Patent Application No. 10-2019-0108924, Jun. 23, 2020.
Notice of Allowance for Korean Patent Application No. 10-2019-0108924, Dec. 9, 2020.
Written Opinion for PCT/KR2019/013539 dated Feb. 5, 2020.
International Search Report for PCT/KR2019/013539, dated Feb. 5, 2020.

*Primary Examiner* — Jennifer E Graser
(74) *Attorney, Agent, or Firm* — Sughrue Mion, PLLC

(57) ABSTRACT

The present specification relates to an astrocyte-specific nucleic acid aptamer and a use thereof. The astrocyte-specific nucleic acid aptamer, according to the disclosure in the present specification, is a DNA aptamer.

3 Claims, 23 Drawing Sheets
Specification includes a Sequence Listing.

Aptamer 1-1: Ast17-30(C)

Aptamer 1-2: Ast13-18(T)

SEQUENCE LISTING

```
<160> NUMBER OF SEQ ID NOS: 12

<210> SEQ ID NO 1
<211> LENGTH: 40
<212> TYPE: DNA
<213> ORGANISM: Artificial Sequence
<220> FEATURE:
<223> OTHER INFORMATION: aptamer

<400> SEQUENCE: 1
tgccgaaggt gccgattgag tgaatcggct gttgtttatg                            40

<210> SEQ ID NO 2
<211> LENGTH: 40
<212> TYPE: DNA
<213> ORGANISM: Artificial Sequence
<220> FEATURE:
<223> OTHER INFORMATION: aptamer

<400> SEQUENCE: 2
tgccgaaggt gccgattgag tgaatcggtt gttgtttatg                            40

<210> SEQ ID NO 3
<211> LENGTH: 40
<212> TYPE: DNA
<213> ORGANISM: Artificial Sequence
```

```
<220> FEATURE:
<223> OTHER INFORMATION: aptamer

<400> SEQUENCE: 3
ggccgacttt ctcttcttta tattttacgg gttctttgtg                              40

<210> SEQ ID NO 4
<211> LENGTH: 40
<212> TYPE: DNA
<213> ORGANISM: Artificial Sequence
<220> FEATURE:
<223> OTHER INFORMATION: aptamer

<400> SEQUENCE: 4
ggccgacttt cttttttca tgtcttacgg gttctttgtg                               40

<210> SEQ ID NO 5
<211> LENGTH: 42
<212> TYPE: DNA
<213> ORGANISM: Artificial Sequence
<220> FEATURE:
<223> OTHER INFORMATION: aptamer

<400> SEQUENCE: 5
ggccggcttt ttcttttctt tatattttat gggttctctg tg                           42

<210> SEQ ID NO 6
<211> LENGTH: 41
<212> TYPE: DNA
<213> ORGANISM: Artificial Sequence
<220> FEATURE:
<223> OTHER INFORMATION: aptamer

<400> SEQUENCE: 6
ggccgacttt tttttttttt atattttacg ggtcctctgt g                            41

<210> SEQ ID NO 7
<211> LENGTH: 40
<212> TYPE: DNA
<213> ORGANISM: Artificial Sequence
<220> FEATURE:
<223> OTHER INFORMATION: aptamer

<400> SEQUENCE: 7
ggccgacttt ttttttttta tattttacgg gtcctctgtg                              40

<210> SEQ ID NO 8
<211> LENGTH: 39
<212> TYPE: DNA
<213> ORGANISM: Artificial Sequence
<220> FEATURE:
<223> OTHER INFORMATION: aptamer

<400> SEQUENCE: 8
ggccaatctt ttttttttat attttacggg tcctttgtg                               39

<210> SEQ ID NO 9
<211> LENGTH: 40
<212> TYPE: DNA
<213> ORGANISM: Artificial Sequence
<220> FEATURE:
<223> OTHER INFORMATION: aptamer

<400> SEQUENCE: 9
ggccaacttt tttcttttt atatttacgg gtcttctgtg                               40
```

```
<210> SEQ ID NO 10
<211> LENGTH: 40
<212> TYPE: DNA
<213> ORGANISM: Artificial Sequence
<220> FEATURE:
<223> OTHER INFORMATION: aptamer

<400> SEQUENCE: 10
ggccgacttt ttctttctta tattttacgt gttttttgtg                             40

<210> SEQ ID NO 11
<211> LENGTH: 40
<212> TYPE: DNA
<213> ORGANISM: Artificial Sequence
<220> FEATURE:
<223> OTHER INFORMATION: aptamer

<400> SEQUENCE: 11
gtagttgtgg tggctacgca tcgtatctgg tgatcagtga                             40

<210> SEQ ID NO 12
<211> LENGTH: 40
<212> TYPE: DNA
<213> ORGANISM: Artificial Sequence
<220> FEATURE:
<223> OTHER INFORMATION: aptamer

<400> SEQUENCE: 12
ttcggtattt ttattctttt ccctgttagg ctagtcctgg                             40
```

ASTROCYTE-SPECIFIC NUCLEIC ACID APTAMER AND USE THEREOF

CROSS REFERENCE TO RELATED APPLICATIONS

This application is a National Stage of International Application No. PCT/KR2019/013539 filed Oct. 15, 2019, claiming priority based on Korean Patent Application No. 10-2018-0122835 filed Oct. 15, 2018.

SEQUENCE LISTING

The content of the electronically submitted sequence listing, file name: Sequence_Listing_As_Filed.txt; size: 2,647 bytes; and date of creation: May 10, 2021, filed herewith, is incorporated herein by reference in its entirety.

TECHNICAL FIELD

A content disclosed by the present specification relates to an astrocyte-specific nucleic acid aptamer and a use thereof, and more specifically, to an astrocyte-specific DNA aptamer.

BACKGROUND ART

Astrocytes are a type of glial cells that make up about 30% of the central nervous system (CNS) of mammals, and are the most common glial cell. Astrocytes support the brain and spinal cord, including the blood-brain barrier, and are also involved in neuronal cell development through the removal of waste products, phagocytosis, the supply of neuronal nutrients, the regulation of ion concentrations, and the like. Further, since it is known that the activity of astrocytes is closely related to the recovery from diseases or damage of the central nervous system, it is important to study astrocytes for the development of therapeutic methods for the central nervous system. In particular, for treatment of the central nervous system, direct conversion methods for specifically differentiating neural stem cells (NSCs) into astrocytes and neurons, differentiating somatic cells into neurons, or differentiating astrocytes into neurons have been reported. Nevertheless, since astrocytes are composed of diverse cells that share similar forms and characteristics in an in vivo environment, a wide range of diversity and heterogeneity are present. It is known that even in active astrocytes that are directly associated with actual treatments or diseases, there is diversity in gene expression patterns, morphology, differentiation, and the like.

DETAILED DESCRIPTION

Technical Challenge

Despite this diversity, a process for confirming astrocytes currently depends on RT-qPCR and immunohistochemistry using biomarkers of genes and protein specifically expressed in astrocytes. As some well-known biomarkers, glial fibrillary acidic protein (GFAP), a glutamate transporter (GLT-1) or a glutamate aspartate transporter (GLAST), aldehyde dehydrogenase 1 family member L1 (Aldh1L1), glutamine synthetase, a calcium-binding protein (S100β), and the like are known. Among them, GFAP has been widely used as a major marker for active astrocytes, but has disadvantages in that GFAP is not present in all astrocytes as an intermediate filament protein present in cells and may stained only in a main stem branch, or may stained in various cells other than astrocytes, and above all, it is impossible to isolate or target astrocytes using GFAP in live astrocytes. Other astrocyte markers also have many problems in specifically recognizing live astrocytes. Therefore, there are no markers and antibodies that can be specifically recognized only in live astrocyte membranes to date, and there is an urgent need for discovering a common marker to study the diversity and function of astrocytes.

Technical Solution

One object of the invention described in the specification is to provide a nucleic acid aptamer that specifically binds to astrocytes.

In one embodiment, the aptamer may have the following configuration.

As an aptamer capable of binding astrocyte, the aptamer may a single strand, wherein the aptamer consists of 80 nucleotides or less, wherein the aptamer comprises at least one stem-loop structure comprises 5'-CCGATT-3' and 5'-AATCGG-3' which are complementarily bound between them, or a loop structure of at least one of the stem-loop structure comprises 15 to 25 nucleotides.

Another object of the invention described in the specification is to provide an aptamer multimer comprising several nucleic acid aptamers that specifically bind to astrocytes.

In one embodiment, the aptamer multimer may have the following configuration.

An aptamer multimer may comprises
  a motif,
  wherein the motif comprises a first single strand comprising a first fragment and a second fragment, and a second single strand comprising a third fragment and a fourth fragment, wherein the second fragment is complementarily bound to the third fragment; and
  a first linker and a first aptamer that is capable of binding astrocyte,
  wherein the first linker is a polynucleotide, wherein the first linker is linked to each other to the first aptamer, wherein the first linker is complementarily bound to the first fragment, wherein the first aptamer is an 80mer or less polynucleotide comprising at least one stem-loop structure; and
  a second linker and a second aptamer that is capable of binding astrocyte, wherein the second linker is a polynucleotide, wherein the second linker is linked to each other to the second aptamer, wherein the second linker is complementarily bound to the fourth fragment, wherein the second aptamer is an 80mer or less polynucleotide comprising at least one stem-loop structure.

Another object of the invention described in the specification is to provide a method for detecting astrocytes using a nucleic acid aptamer.

In one embodiment, the method may be a sensor for detecting astrocytes comprising at least one of the aptamer or aptamer multimer.

Another object thereof is to provide a composition for diagnosing or treating astrocytes using a nucleic acid aptamer.

To achieve the objects, the present invention provides a nucleic acid aptamer that includes any one nucleic acid sequence selected from the group consisting of nucleic acid sequences represented by SEQ ID Nos: 1 to 10 and can specifically bind to astrocytes.

Further, the present invention provides a method for detecting astrocytes, which includes using the above nucleic acid aptamer, a nucleic acid aptamer including a chemical modification thereof, or a nucleic acid aptamer including a biological modification thereof.

In addition, the present invention provides a method for diagnosing or treating astrocytes, which includes using the above nucleic acid aptamer, a nucleic acid aptamer including a chemical modification thereof, or a nucleic acid aptamer including a biological modification thereof.

Furthermore, the present invention provides a kit for diagnosing or detecting astrocytes, the kit containing the above nucleic acid aptamer or a nucleic acid aptamer including a modification thereof.

Further, the present invention provides a method for detecting astrocytes, which includes using the sensor or kit for diagnosing or detecting astrocytes.

The sensor or kit is not a fixed form, but is a concept including all types of objects capable of diagnosing or detecting astrocytes.

Advantageous Effects

A single stranded DNA aptamer has high binding strength and specificity to astrocytes which are target cells, completes a reaction within a short time, and is structurally more stable than antibodies, so that it is expected that a device, sensor, or kit for detecting astrocytes can be more easily made and used. In addition, it is expected that the single stranded DNA aptamer can also be used for a technique for isolating only astrocytes by astrocyte-specific binding.

MODES OF THE INVENTION

Figure 1:
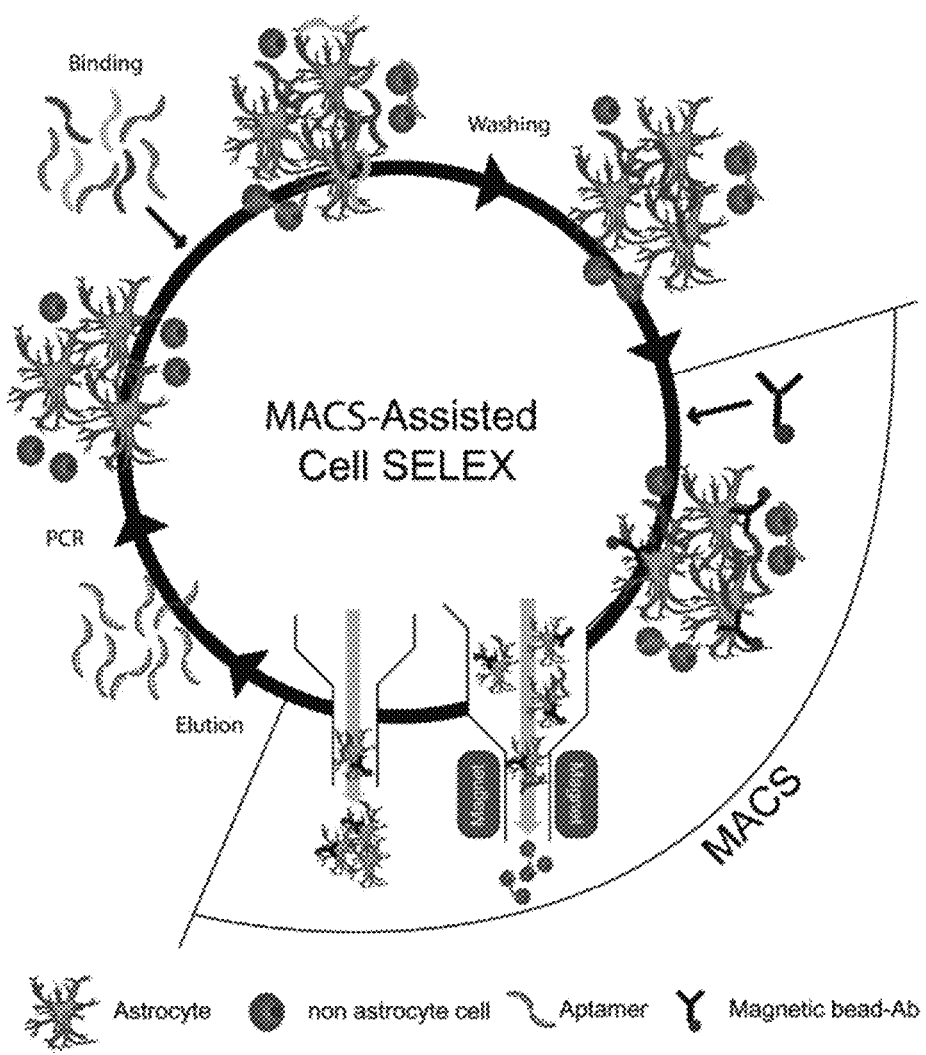
FIG. 1 illustrates an overview of magnetic activated cell sorting (MACS)-assisted systematic evolution of ligands by exponential enrichment (SELEX) according to an exemplary embodiment.

Various terms will be defined in the present specification to describe the content disclosed in the present specification. In addition to these terms, other terms, if necessary, are defined elsewhere in the present specification. Unless otherwise explicitly defined in the present specification, the terms used herein will have meanings recognized in the art. When conflicting, the meanings may be interpreted by the definition of the present specification.

The term 'about' refers to an amount, a level, a value, a number, a frequency, a percentage, a dimension, a size, a quantity, a weight, or a length that varies to the degree of 30, 25, 20, 15, 10, 9, 8, 7, 6, 5, 4, 3, 2, or 1% with respect to a reference amount, level, value, number, frequency, percentage, dimension, size, quantity, weight, or length.

Hereinafter, the content disclosed by the present specification will be described in detail.

Aptamer

The term "aptamer" refers to a sequence capable of specifically and strongly binding to a specific target molecule or target cell, and a nucleic acid having a three-dimensional structure of the sequence.

A DNA aptamer refers to a DNA nucleic acid molecule capable of binding to a specific molecule or cell with high affinity and specificity, and refers to a single- or double stranded DNA nucleic acid molecule.

A RNA aptamer refers to a RNA nucleic acid molecule capable of binding to a specific molecule or cell with high affinity and specificity, and refers to a single- or double stranded RNA nucleic acid molecule.

As an exemplary embodiment of the invention disclosed by the specification, an aptamer may be a sequence which has a characteristic of being able to specifically bind to astrocytes or live astrocytes, and has a number of nucleotides between any two numbers selected from 10, 20, 30, 40, 50, 60, 70 or 80, which is a relatively short length.

As an exemplary embodiment of the invention disclosed by the specification, an aptamer may have one, two, three, or four or more stem structures.

As an exemplary embodiment of the invention disclosed by the specification, an aptamer may have one, two, three, or four or more loop structures.

As an exemplary embodiment of the invention disclosed by the specification, an aptamer may have one, two, three, or four or more stem-loop structures.

The aforementioned stem-loop structure includes a stem structure and a loop structure.

As a specific embodiment, each stem-loop structure of an aptamer having a plurality of stem-loop structures may be the same or different.

As a specific embodiment, the length of the base sequence of each stem-loop structure of an aptamer having a plurality of stem-loop structures may be the same or different. As a specific embodiment, each stem structure or loop structure of an aptamer having a plurality of stem-loop structures may be the same or different.

Compared to an antibody, an aptamer has various advantages such as:

(1) Since the aptamer is a molecule which is easily chemically synthesized and is also relatively small and simple, various necessary modifications are possible.
(2) Selectivity and affinity can be maximized through a systematic evolution of ligands by exponential enrichment (SELEX) process.
(3) Purity is high because the aptamer is made by chemical synthesis.
(4) It is possible to develop an aptamer for a toxin and the like which are difficult to inject into animals to produce antibodies.
(5) The aptamer is stable against heat and can be stored at room temperature for a long time.
(6) The aptamer rarely causes an in vivo immune response.

The sequence of the aptamer may be, for example, a nucleic acid sequence developed by evolutionary molecular engineering. An aptamer that strongly binds to the target molecule can be purified using SELEX technology.

SELEX is a process of deriving an aptamer that targets a specific molecule in a polynucleotide library which is a large collection of random sequences. In SELEX, after sequences that do not bind to a target molecule are removed by allowing a polynucleotide library to react with a target molecule and sequences binding to the target molecule are isolated and amplified through a polymerase chain reaction (PCR), only sequences that most strongly bind to the target molecule is finally selected as an aptamer candidate group by repeating the previous process several times.

As a specific embodiment, dsDNA is synthesized by DNA polymerase by collecting polynucleotides binding to the target molecule, and then single stranded polynucleotides are amplified by performing PCR using the dsDNA as a template for asymmetric PCR, thereby finally selecting only a sequence which is highly likely to most strongly bind to the target as an aptamer candidate.

As an exemplary embodiment of the invention disclosed by the specification, the SELEX can use a method known in the art, and specific examples thereof include Cell-SELEX, but are not limited thereto. As an exemplary embodiment of the invention disclosed by the specification, the Cell-SELEX technique may be performed in combination with other techniques. As a specific embodiment, MACS-assisted SELEX may be performed by combining the Cell-SELEX technique and the MACS technique.

As an exemplary embodiment of the invention disclosed by the specification, an aptamer may be represented by the following SEQ ID Nos: 1 to 10.

```
Aptamer 1-1:
                              (SEQ ID NOs: 1)
TGCCGAAGGTGCCGATTGAGTGAATCGGCTGTTGTTTATG Aptamer 1-2:
                              (SEQ ID NOs: 2)
TGCCGAAGGTGCCGATTGAGTGAATCGGTTGTTGTTTATG Aptamer 2:
                              (SEQ ID NOs: 3)
GGCCGACTTTCTCTTCTTTATATTTTACGGGTTCTTTGTG Aptamer 3:
                              (SEQ ID NOs: 4)
GGCCGACTTTCTTTTTTTCATGTCTTACGGGTTCTTTGTG Aptamer 4:
                              (SEQ ID NOs: 5)
GGCCGGCTTTTTCTTTTCTTTATATTTTATGGGTTCTCTGTG Aptamer 5:
                              (SEQ ID NOs: 6)
GGCCGACTTTTTTTTTTTTATATTTTACGGGTCCTCTGTG Aptamer 6:
                              (SEQ ID NOs: 7)
GGCCGACTTTTTTTTTTTATATTTTACGGGTCCTCTGTG Aptamer 7:
                              (SEQ ID NOs: 8)
GGCCAATCTTTTTTTTTATATTTTACGGGTCCTTTGTG Aptamer 8:
                              (SEQ ID NOs: 9)
GGCCAACTTTTTCTTTTTATATTTACGGGTCTTCTGTG Aptamer 9:
                              (SEQ ID NOs: 10)
GGCCGACTTTTTCTTTCTTATATTTTACGTGTTTTTGTG Scramble Aptamer 1:
                              (SEQ ID NOs: 11)
GTAGTTGTGGTGGCTACGCATCGTATCTGGTGATCAGTGA Scramble Aptamer 2:
                              (SEQ ID NOs: 12)
TTCGGTATTTTATTCTTTTCCCTGTTAGGCTAGTCCTGG
```

The scrambled aptamer 1 and scramble aptamer 2 refer to a negative control of the aptamer 1 and aptamer 2, respectively.

Based on the base sequences of the above aptamers, they are organized into two groups as shown in the table below.

The number shown in the Frequency is the number of occurrences of the aptamer sequence belonging to the group.

TABLE 1

| Group | ID | Frequency | Sequence |
|---|---|---|---|
| 1 | #17-30 | 31 | TGCCGAAGGTGCCGATTGAGTGAATCGGCTGTTGTTTATG |
|  | #12-10 |  | TGCCGAAGGTGCCGATTGAGTGAATCGGTTGTTGTTTATG |
|  | #12-18 |  | TGCCGAAGGTGCCGATTGAGTGAATCGGTTGTTGTTTATG |
| 2 | #12-22 | 11 | GGCCGACTTTCTTTTTTTCATGTCTTACGGGTTCTTTGTG |
|  | #13-12 |  | GGCCGGCTTTTTCTTTTCTTTATATTTTATGGGTTCTCTGTG |
|  | #13-13 |  | GGCCGACTTTCTCTTCTTTATATTTTACGGGTTCTTTGTG |
|  | #13-17 |  | GGCCGACTTTTTTTTTTTTATATTTTACGGGTCCTCTGTG |

TABLE 1-continued

| Group ID | Frequency | Sequence |
|---|---|---|
| #13-22 | | GGCCGACTTTTTTTTTTTATATTTTACGGGTCCTCTGTG |
| #13-32 | | GGCCAATCTTTTTTTTTTATATTTTACGGGTCCTTTGTG |
| #13-67 | | GGCCGACTTTCTCTTCTTTATATTTTACGGGTTCTTTGTG |
| #13-69 | | GGCCAACTTTTTCTTTTTTATATTTACGGGTCTTCTGTG |
| #17-48 | | GGCCGACTTTTTCTTTCTTATATTTTACGTGTTTTTTGTG |

It is possible to provide a nucleic acid sequence having homology between any two numbers selected from about 70, about 75, about 80, about 85, about 90, about 91, about 92, about 93, about 94, about 95, about 96, about 97, about 98, about 99, or about 100% with any one nucleic acid sequence among the nucleic acid sequences represented by SEQ ID Nos: 1 to 10 by a change in the nucleotide sequences.

As an exemplary embodiment of the invention disclosed by the specification, an aptamer including a polynucleotide may be provided as a chemically or structurally modified aptamer. Those skilled in the art can easily carry out various modifications such as change in the nucleotide sequence of the aptamer, chemical residue substitution, or attachment of a functional polymer.

As an exemplary embodiment, in the case of the RNA aptamer, stability may be enhanced by substituting ribose 2'-OH with a 2'-F, 2'-NH2 or 2'-O-methyl group in order to overcome the instability of the molecule. The invention described in the specification is not limited to the above examples and includes all substitutions which may be taken by those skilled in the art to enhance the stability of the molecule.

As an exemplary embodiment, a polymer such as PEG, albumin, or cholesterol may be bound to a nucleic acid aptamer to increase the in vivo half-life or stability of the nucleic acid aptamer. The invention described in the specification is not limited to the above examples and includes all types of polymer binding taken by those skilled in the art to enhance the half-life or stability of the molecule.

The above-mentioned modification of the nucleotide sequence includes those having a sequence different from that before the modification due to insertion, deletion, inversion, substitution or binding thereof of one or more nucleic acids artificially or naturally within the nucleic acid sequence constituting the gene.

As an exemplary embodiment of the invention disclosed by the specification, an astrocyte-specific nucleic acid aptamer may be provided.

The astrocyte-specific refers to the recognition of an astrocyte-labeled protein or peptide. More specifically, the astrocyte-specific refers to the recognition of a protein or peptide on the surface of astrocytes, a protein or peptide immobilized on the cell membrane of astrocytes, or a protein or peptide penetrating the cell membrane of astrocytes.

The "astrocyte-specific" refers to being capable of binding to a labeled protein or a labeled peptide on the surface of astrocytes.

As an exemplary embodiment of the invention disclosed by the specification, the aptamer may be a DNA aptamer.

As an exemplary embodiment of the invention disclosed by the specification, the DNA aptamer may be a nucleic acid aptamer specific for live astrocytes.

As an exemplary embodiment, as a nucleic acid aptamer specific for live astrocytes, aptamers having sequences of SEQ ID Nos: 1 to 10 may be provided.

As an exemplary embodiment, the nucleic acid aptamer specific for live astrocytes may be obtained by subjecting a sequence of a DNA aptamer to various modifications such as chemical residue substitution or attachment of a functional polymer.

As an exemplary embodiment, the nucleic acid aptamer specific for live astrocytes may include an effective moiety that specifically binds to a target molecule or target cell.

As an exemplary embodiment, the nucleic acid aptamer specific for live astrocytes may include a stem-loop structure.

As an exemplary embodiment of the invention disclosed by the specification, the aptamer may be a RNA aptamer.

As an exemplary embodiment of the invention disclosed by the specification, the RNA aptamer may be a nucleic acid aptamer specific for live astrocytes.

As an exemplary embodiment, the RNA aptamer may be a RNA aptamer in which T is substituted for U in a DNA aptamer having sequences of SEQ ID Nos: 1 to 10.

As an exemplary embodiment, the nucleic acid aptamer specific for live astrocytes may be obtained by subjecting a sequence of a RNA aptamer to various modifications such as chemical residue substitution or attachment of a functional polymer.

As an exemplary embodiment, the nucleic acid aptamer specific for live astrocytes may include an effective moiety that specifically binds to a target molecule or target cell.

As an exemplary embodiment, the nucleic acid aptamer specific for live astrocytes may include a stem-loop structure.

Aptamer Multimer

As an exemplary embodiment of the invention disclosed by the specification, an aptamer multimer including several aptamers may be provided.

As an exemplary embodiment, the aptamer multimer may include an aptamer subjected to various modifications such as chemical residue substitution or attachment of a functional polymer or linker to a sequence of the aptamer.

As an exemplary embodiment of the invention disclosed by the specification, an aptamer multimer in which each of the several aptamers described above is bound to a specific motif may be provided.

As an exemplary embodiment of the invention disclosed by the specification, the motif refers to anything having a structure which can be used to prepare an aptamer multimer.

As an exemplary embodiment, the motif may be a nucleotide complex, polypeptide, or protein.

Further, as an exemplary embodiment, the motif may be any motif that can be naturally realized by those skilled in the art such that several aptamers can be bound without being limited to a specific structure or material.

As an exemplary embodiment of the invention disclosed by the specification, the nucleotide complex that constitutes the motif may be a complex of single stranded DNA or single stranded RNA.

As an exemplary embodiment, the motif may include only single stranded DNA.

As an exemplary embodiment, the motif may include only single stranded RNA.

As an exemplary embodiment, the motif may include a combination of single stranded DNA or RNA.

As an exemplary embodiment, the single stranded DNA or RNA may be artificially prepared or naturally obtained. As an example, a part of each single stranded DNA or RNA constituting the motif may be complementarily bound to each other. In addition, as an example, a part of each single stranded DNA or RNA constituting the motif may be complementarily bound to each other to prepare a motif to which several aptamers may be bound.

As an exemplary embodiment, two, three, four, five, or six or more single stranded DNAs or RNAs may be bound to each other to form a motif.

As an exemplary embodiment, a motif including two single stranded DNAs or RNAs may bind one, two, or three or more aptamers.

As an exemplary embodiment, a motif including three single stranded DNAs or RNAs may bind one, two, three, or four or more aptamers.

As an exemplary embodiment, a motif including four single stranded DNAs or RNAs may bind one, two, three, four, or five or more aptamers.

As an exemplary embodiment, a motif including five single stranded DNAs or RNAs may bind one, two, three, four, five, or six or more aptamers.

As an exemplary embodiment, a motif including six single stranded DNAs or RNAs may bind one, two, three, four, five, six, or seven or more aptamers.

The aptamers that bind to the motif may be the same or different from each other.

The aptamers that bind to the motif may all be the same aptamer.

The aptamers that bind to the motif may all be different aptamers.

The aptamers that bind to the motif may only be partially identical.

As an exemplary embodiment of the invention disclosed by the specification, a combination of two single stranded DNAs or RNAs may provide a motif for preparing an aptamer dimer.

As an exemplary embodiment, the two single strands may be the same or different from each other.

As an exemplary embodiment of the invention disclosed by the specification, a combination of three single stranded DNAs or RNAs may provide a motif for preparing an aptamer dimer or trimer. As an exemplary embodiment, the three single strands may be the same, only partially identical, or all different.

As an exemplary embodiment of the invention disclosed by the specification, a combination of N single stranded DNAs or RNAs may provide a motif for preparing an aptamer dimer, trimer, tetramer, or N-mer. In this case, the N means any one of two or more integers. The N single strands may be the same, only partially identical, or all different.

As an exemplary embodiment of the invention disclosed by the specification, it is possible to provide an aptamer multimer in which a linker and an aptamer bind to the motif for preparing the dimer aptamer.

Figure 21:
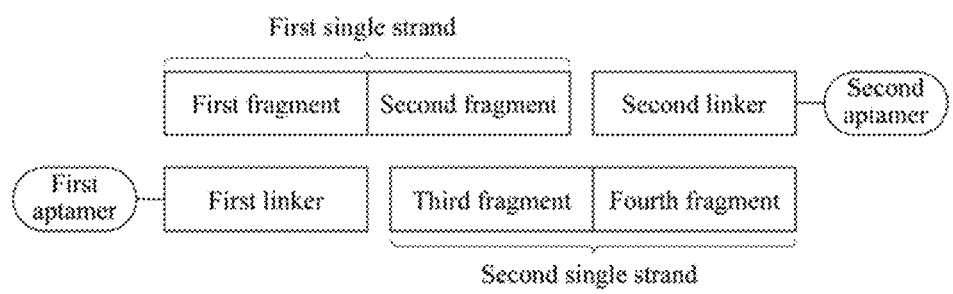
FIGS. 21 and 23 illustrate a structure of an aptamer mutimer according to an exemplary embodiment.

As a representative example, the aptamer multimer schematically illustrated in FIG. 21 may be provided. Based on this, an aptamer multimer will be described below.

As an exemplary embodiment of the invention disclosed by the specification, a motif for preparing an aptamer dimer may be provided. As an exemplary embodiment, the motif for preparing the aptamer dimer may include several single stranded DNAs or RNAs including two or more fragments.

As an example, the motif may include a first single stranded DNA including a first fragment and a second fragment and a second single stranded DNA including a third fragment and a fourth fragment (FIG. 21).

As an example, the second fragment may have a sequence complementary to or complementarily bind to the third fragment.

As an example, the first fragment and the fourth fragment may have the same sequence or different sequences.

As an example, the first linker may be single stranded DNA or RNA, a polypeptide, or a protein.

As an example, the first fragment and the first linker may be linked to each other.

As an example, the first fragment and the first linker may have a sequence complementary to each other, or may be complementary to each other.

As an example, the first fragment and the first linker may be directly or indirectly linked to each other.

As an example, the first fragment and the first linker may be linked to each other by a covalent bond, a non-covalent bond, or an intermolecular bond.

As an example, the first linker may be linked to a first aptamer. As an example, the first linker and the first aptamer may have a sequence complementary to each other, or may be complementary to each other.

As an example, the first linker and the first aptamer may be directly or indirectly linked to each other.

As an example, the first linker and the first aptamer may be linked to each other by a covalent bond, a non-covalent bond, or an intermolecular bond.

As an exemplary embodiment of the invention disclosed by the specification, it may be provided that the first fragment, the first linker, and the first aptamer are linked.

As an exemplary embodiment of the invention disclosed by the specification, a second linker and a second aptamer may be further included in the motif to which the first linker and the first aptamer are linked.

As an example, the second linker may be single stranded DNA or RNA, a polypeptide, or a protein.

As an example, the fourth fragment and the second linker may be linked to each other.

As an example, the fourth fragment and the second linker may have a sequence complementary to each other, or may be complementary to each other.

As an example, the fourth fragment and the second linker may be directly or indirectly linked to each other.

As an example, the fourth fragment and the second linker may be linked to each other by a covalent bond, a non-covalent bond, or an intermolecular bond.

As an example, the second linker may be linked to a second aptamer.

As an example, the second linker and the second aptamer may have a sequence complementary to each other, or may be complementary to each other.

As an example, the second linker and the second aptamer may be directly or indirectly linked to each other.

As an example, the second linker and the second aptamer may be linked to each other by a covalent bond, a non-covalent bond, or an intermolecular bond.

As an exemplary embodiment of the invention disclosed by the specification, it may be provided that the fourth fragment, the second linker, and the second aptamer are linked.

As an exemplary embodiment of the invention disclosed by the specification, it is possible to provide an aptamer dimer in which the first fragment of the motif, the first linker, and the first aptamer are linked and the fourth fragment of the motif, the second linker, and the second aptamer are linked.

Figure 22:
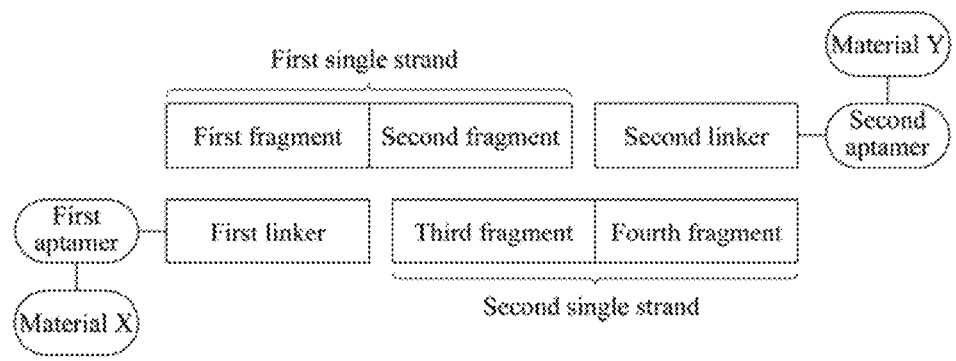
FIGS. 22 and 24 illustrate a structure in which an aptamer multimer according to an exemplary embodiment and a specific material are bound.

As an exemplary embodiment of the invention disclosed by the specification, an aptamer having the configuration illustrated in FIG. 22 may be provided. Hereinafter, the aptamer will be described below based on this.

As an exemplary embodiment of the invention disclosed by the specification, it may be provided that a specific material binds to an aptamer multimer.

As an exemplary embodiment, it may be provided that a specific material binds to the aptamer dimer.

As an example, the materials binding to the first or second aptamer may be the same or different material. Further, no material may bind to the first aptamer and the second aptamer.

As an example, the material binding to the aptamer may be an imaging agent.

The imaging agent refers to a material which has a characteristic of being able to emit light by itself, or has a characteristic of being specifically detected by a specific device, and may be, for example, a contrast medium, an inorganic sulfide, an oxide, a halide, and a fluorescent protein as a biological marker. The fluorescent protein may be a green fluorescent protein (GFP), a red fluorescent protein (RFP), a blue fluorescent protein (BFP), or a cyan fluorescent protein (CFP).

The invention disclosed by the present specification is not limited to the above materials, and all imaging agents that can be easily adopted by those skilled in the art may be bound to the aptamer.

As an example, the material binding to the aptamer may be a material that has a function of enhancing in vivo half-life or stability. For example, a material having a function of enhancing in vivo half-life or stability may be PEG, albumin, cholesterol or the like. The invention disclosed by the present specification is not limited to these materials, and all materials that can be easily adopted by those skilled in the art and have a function of enhancing in vivo half-life or stability may be bound to the aptamer.

As an example, the material binding to the aptamer includes a therapeutic agent, an antibody, a protein, an enzyme or the like having a therapeutic function in the body. The invention disclosed by the present specification is not limited to these materials, and all materials that can be easily adopted by those skilled in the art and have a therapeutic function in the body may be bound to the aptamer. Furthermore, for the function, the material binding to the aptamer may be a therapeutic agent, an antibody, a protein, an enzyme or the like having a therapeutic function not only in the human body, but also in a non-human body. The non-human refers to all animals having astrocytes such as vertebrates and invertebrates, specifically mammals, primates, and rodents other than humans.

As an exemplary embodiment of the invention disclosed by the specification, a motif for preparing an aptamer trimer may be provided.

Figure 23:
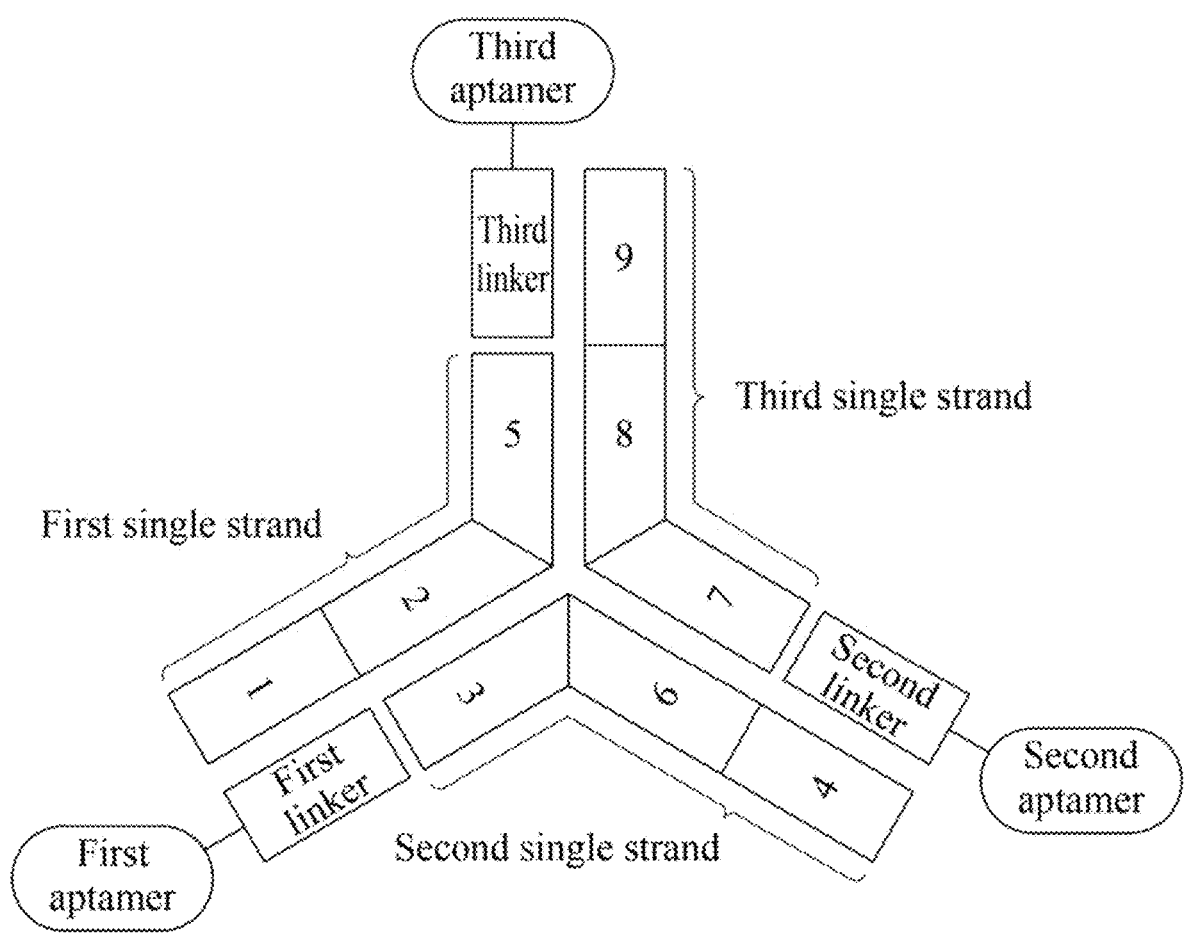

As an exemplary embodiment of the invention disclosed by the specification, an aptamer trimer having the configuration illustrated in FIG. 23 may be provided. Hereinafter, the aptamer trimer will be described below based on this.

As an exemplary embodiment, the motif for preparing the aptamer trimer may include three or more single stranded DNAs or RNAs including three or more fragments.

As an exemplary embodiment, the motif may include a first single stranded DNA or RNA including a first fragment, a second fragment, and a fifth fragment,
a second single stranded DNA or RNA including a third fragment, a fourth fragment, and a sixth fragment, and
a third single stranded DNA or RNA including a seventh fragment, an eighth fragment, and a ninth fragment.

The second fragment may have a sequence complementary to the third fragment, or may be complementary to the third fragment.

The fifth fragment may have a sequence complementary to the eighth fragment, or may be complementary to the eighth fragment. The sixth fragment may have a sequence complementary to the seventh fragment, or may be complementary to the seventh fragment. As an example, the first fragment and the fourth fragment may have the same sequence or different sequences.

As an example, the first fragment and the ninth fragment may have the same sequence or different sequences.

As an example, the fourth fragment and the ninth fragment may have the same sequence or different sequences.

As an exemplary embodiment of the invention disclosed by the specification, it is possible to provide an aptamer multimer in which linkers and aptamers are bound to the motif for preparing the trimer aptamer.

As an example, the first linker may be single stranded DNA or RNA, a polypeptide, or a protein.

As an example, the first fragment and the first linker may be linked to each other. As an example, the first fragment and the first linker may have a sequence complementary to each other, or may be complementary to each other. As an example, the first fragment and the first linker may be directly or indirectly linked to each other. As an example, the first fragment and the first linker may be linked to each other by a covalent bond, a non-covalent bond, or an intermolecular bond.

As an example, the first linker may be linked to a first aptamer. As an example, the first linker and the first aptamer may have a sequence complementary to each other, or may be complementary to each other. As an example, the first linker and the first aptamer may be directly or indirectly linked to each other. As an example, the first linker and the first aptamer may be linked to each other by a covalent bond, a non-covalent bond, or an intermolecular bond. As an exemplary embodiment of the invention disclosed by the specification, it may be provided that the first fragment, the first linker, and the first aptamer are linked.

As an exemplary embodiment of the invention disclosed by the specification, a second linker and a second aptamer may be further included in the motif to which the first linker and the first aptamer are linked.

As an example, the second linker may be single stranded DNA or RNA, a polypeptide, or a protein.

As an example, the fourth fragment and the second linker may be linked to each other. As an example, the fourth fragment and the second linker may have a sequence complementary to each other, or may be complementary to each other. As an example, the fourth fragment and the second linker may be directly or indirectly linked to each other. As an example, the fourth fragment and the second linker may be linked to each other by a covalent bond, a non-covalent bond, or an intermolecular bond.

As an example, the second linker may be linked to a second aptamer. As an example, the second linker and the second aptamer may have a sequence complementary to each other, or may be complementary to each other. As an example, the second linker and the second aptamer may be directly or indirectly linked to each other. As an example, the second linker and the second aptamer may be linked to each other by a covalent bond, a non-covalent bond, or an intermolecular bond.

As an exemplary embodiment of the invention disclosed by the specification, it may be provided that the fourth fragment, the second linker, and the second aptamer are linked.

As an exemplary embodiment of the invention disclosed by the specification, it is possible to provide an aptamer dimer in which the first fragment of the motif, the first linker, and the first aptamer are linked, and
the fourth fragment of the motif, the second linker, and the second aptamer are linked.

As an exemplary embodiment of the invention disclosed by the specification, it is possible to provide an aptamer multimer in which a linker and an aptamer bind to the motif for preparing the dimer aptamer (FIG. 23).

As an exemplary embodiment of the invention disclosed by the specification, a third linker and a third aptamer may be further included in an aptamer dimer in which the first fragment of the motif, the first linker, and the first aptamer are linked, and
the fourth fragment of the motif, the second linker, and the second aptamer are linked.

As an example, the third linker may be single stranded DNA or RNA, a polypeptide, or a protein.

As an example, the ninth fragment and the third linker may be linked to each other. As an example, the ninth fragment and the third linker may have a sequence complementary to each other, or may be complementary to each other. As an example, the ninth fragment and the third linker may be directly or indirectly linked to each other. As an example, the ninth fragment and the third linker may be linked to each other by a covalent bond, a non-covalent bond, or an intermolecular bond.

As an example, the third linker may be linked to a third aptamer. As an example, the third linker and the third aptamer may have a sequence complementary to each other, or may be complementary to each other. As an example, the third linker and the third aptamer may be directly or indirectly linked to each other. As an example, the third linker and the third aptamer may be linked to each other by a covalent bond, a non-covalent bond, or an intermolecular bond.

As an exemplary embodiment of the invention disclosed by the specification, it may be provided that the ninth fragment, the third linker, and the third aptamer are linked.

As an exemplary embodiment of the invention disclosed by the specification, it is possible to provide an aptamer trimer in which the first fragment of the motif, the first linker, and the first aptamer are linked,
the fourth fragment of the motif, the second linker, and the second aptamer are linked, and
the ninth fragment of the motif, the third linker, and the third aptamer are linked.

As an exemplary embodiment of the invention disclosed by the specification, an aptamer multimer using a motif for preparing the trimer aptamer may have a configuration described in FIG. 23.

Figure 24:
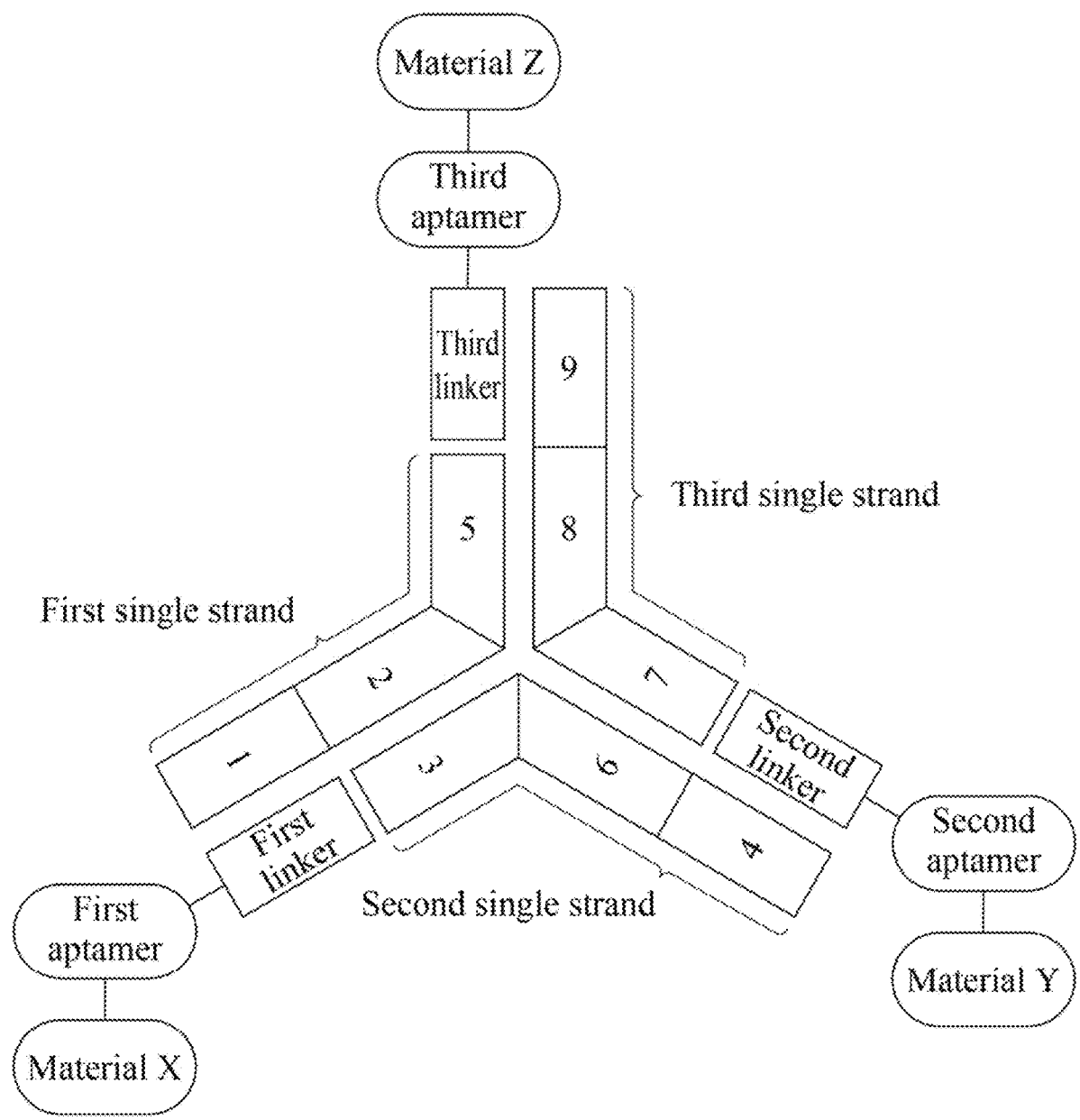

In other exemplary embodiments, it is possible to provide a specific material binding to an aptamer multimer using the motif for preparing the trimer aptamer. As an example, the aptamer multimer may have a configuration described in FIG. 24.

As an example, the materials binding to the first aptamer, the second aptamer, or the third aptamer may be the same or different material. Further, no material may be bound to any one or more of the aptamers.

As an example, the material binding to the aptamer may be an imaging agent.

The imaging agent refers to a material which has a characteristic of being able to emit light by itself, or has a characteristic of being specifically detected by a specific device, and may be, for example, a contrast medium, an inorganic sulfide, an oxide, a halide, and a fluorescent protein as a biological marker. The fluorescent protein may be a green fluorescent protein (GFP), a red fluorescent protein (RFP), a blue fluorescent protein (BFP), or a cyan fluorescent protein (CFP).

The invention disclosed by the present specification is not limited to the above materials, and all materials having characteristics of an imaging agent that can be easily adopted by those skilled in the art may be bound to the aptamer.

As an example, the material binding to the aptamer may be a material that has a function of enhancing in vivo half-life or stability. For example, a material having a function of enhancing in vivo half-life or stability may be PEG, albumin, cholesterol or the like. The invention disclosed by the present specification is not limited to these materials, and all materials that can be easily adopted by those skilled in the art and have a function of enhancing in vivo half-life or stability may be bound to the aptamer.

As an example, the material binding to the aptamer includes a therapeutic agent, an antibody, a protein, an enzyme or the like having a therapeutic function in the body. The invention disclosed by the present specification is not limited to these materials, and all materials that can be easily adopted by those skilled in the art and have a therapeutic function in the body may be bound to the aptamer. Furthermore, for the function, the material binding to the aptamer may be a therapeutic agent, an antibody, a protein, an enzyme or the like having a therapeutic function not only in the human body, but also in a non-human body. The non-humans refer to mammals, primates, and the like other than humans.

Aptamer Conjugate or Composition

As an exemplary embodiment of the invention disclosed by the specification, an aptamer conjugate may be provided.

The aptamer conjugate refers to a conjugate in which a material having a function of enhancing in vivo half-life or stability, an imaging agent, a material having a therapeutic function, or the like is directly bound to an aptamer or an aptamer multimer, or indirectly linked to the aptamer or the aptamer multimer via a linker.

As an example, the material binding to the aptamer may be an imaging agent.

The imaging agent refers to a material which has a characteristic of being able to emit light by itself, or has a characteristic of being specifically detected by a specific device, and may be, for example, a contrast medium, an inorganic sulfide, an oxide, a halide, and a fluorescent protein as a biological marker. The fluorescent protein may be a green fluorescent protein (GFP), a red fluorescent protein (RFP), a blue fluorescent protein (BFP), or a cyan fluorescent protein (CFP).

The invention disclosed by the present specification is not limited to the above materials, and all materials having characteristics of an imaging agent that can be easily adopted by those skilled in the art may be bound to the aptamer.

As an example, the material binding to the aptamer may be a material that has a function of enhancing in vivo half-life or stability. For example, a material having a function of enhancing in vivo half-life or stability may be PEG, albumin, cholesterol or the like. The invention disclosed by the present specification is not limited to these materials, and all materials that can be easily adopted by those skilled in the art and have a function of enhancing in vivo half-life or stability may bind to the aptamer.

As an example, the material binding to the aptamer includes a therapeutic agent, an antibody, a protein, an enzyme or the like having a therapeutic function in the body. The invention disclosed by the present specification is not limited to these materials, and all materials that can be easily adopted by those skilled in the art and have a therapeutic function in the body may be bound to the aptamer. Furthermore, for the function, the material binding to the aptamer may be a therapeutic agent, an antibody, a protein, an enzyme or the like having a therapeutic function not only in the human body, but also in the non-human body. The non-humans refer to mammals, primates, and the like other than humans.

As an example, the aptamer conjugate may be used to detect a specific molecule or cell.

As an example, the aptamer conjugate may be used to diagnose or treat a specific molecule or a specific cell.

As an example, the specific cell may be an astrocyte.

As an example, the specific cell may be a live astrocyte.

As an exemplary embodiment of the invention disclosed by the specification, it is possible to provide a pharmaceutical composition including an aptamer, an aptamer multimer, or an aptamer conjugate as an active ingredient.

The pharmaceutical composition may include any material that can be easily used by those skilled in the art.

Method for Preparing Aptamer

According to another aspect disclosed by the present specification, it is possible to provide a method for synthesizing a nucleic acid aptamer, an aptamer multimer or an aptamer conjugate which specifically recognizes astrocytes.

The method for synthesizing a nucleic acid aptamer may be in vitro synthesis. For example, the in vitro synthesis may be synthesis using a polymerase chain reaction (PCR). However, the method is not limited to this method, and includes all methods that can be adopted by those skilled in the art such that the nucleic acid aptamer can be easily synthesized.

The method for synthesizing a nucleic acid aptamer may be intracellular synthesis.

The intracellular synthesis method may be synthesis from a bioreactor. However, the method is not limited to this method, and includes all methods that can be adopted by those skilled in the art such that the nucleic acid aptamer can be easily synthesized.

The aptamer multimer may be synthesized in vitro.

For example, the in vitro synthesis method may be a method of synthesizing the aptamer multimer by putting the aptamer and the motif in a high temperature reactor and boiling the resulting mixture, and then allowing the mixture to react while lowering the temperature. However, the method is not limited to this method, and includes all methods that can be adopted by those skilled in the art such that the nucleic acid aptamer can be easily synthesized.

Use of Aptamer

As an exemplary embodiment of the invention disclosed by the specification, it is possible to provide a use of a nucleic acid aptamer that specifically binds to or recognizes astrocytes.

As an exemplary embodiment of the invention disclosed by the specification, it is possible to provide a use of an aptamer multimer that specifically binds to or recognizes astrocytes.

As an exemplary embodiment of the invention disclosed by the specification, it is possible to provide a use of an aptamer conjugate that specifically binds to or recognizes astrocytes.

As an exemplary embodiment of the invention disclosed by the specification, it is possible to provide a use of a pharmaceutical composition including an aptamer, an aptamer multimer, or an aptamer conjugate that specifically binds to or recognizes astrocytes as an active ingredient.

As an exemplary embodiment of the invention disclosed by the specification, the use may be provided for labeling an astrocyte using an aptamer.

As an example, an imaging agent may be bound to an aptamer, an aptamer multimer, or an aptamer conjugate.

The imaging agent refers to a material which has a characteristic of being able to emit light by itself, or has a characteristic of being specifically detected by a specific device, and may be, for example, a contrast medium, an inorganic sulfide, an oxide, a halide, and a fluorescent protein as a biological marker. The fluorescent protein may be a green fluorescent protein (GFP), a red fluorescent protein (RFP), a blue fluorescent protein (BFP), or a cyan fluorescent protein (CFP).

The invention disclosed by the present specification is not limited to the above materials, and all materials having characteristics of an imaging agent that can be easily adopted by those skilled in the art may bind to the aptamer.

As an exemplary embodiment of the invention disclosed by the specification, the use may be provided for delivering a specific material to astrocytes using an aptamer.

As an example, a use of delivering a specific material to live astrocytes may be provided by coating the surface of a polymer or nanoparticle with an aptamer.

As an exemplary embodiment of the invention disclosed by the specification, it is possible to provide a use of diagnosing and/or detecting astrocytes using an aptamer.

In the diagnosis or detection, a sensor, a kit, or the like may be used.

As an exemplary embodiment of the invention disclosed by the specification, it is possible to provide a use of isolating astrocytes using an aptamer.

As an exemplary embodiment of the invention disclosed by the specification, it is possible to provide a use of treating astrocytes using an aptamer.

The use of treating astrocytes may use an aptamer for use as a therapeutic agent.

The use of treating astrocytes may be for the development of a therapeutic agent using an aptamer-drug conjugate.

As an exemplary embodiment of the invention disclosed by the specification, a use of screening a therapeutic agent may be provided.

Hereinafter, the present specification will be described in more detail through Examples.

In the following Examples, the term "include" or "have" is intended to indicate the presence of a characteristic, number, step, operation, constituent element, part or any combination thereof described in the specification, and it should be understood that the possibility of the presence or addition of one or more other characteristics or numbers, steps, operations, constituent elements, parts or any combination thereof is not precluded.

These Examples are only for exemplifying the content disclosed by the present specification, and it will be obvious to those skilled in the art that the scope of the content disclosed by the present specification should not be interpreted as being limited by these Examples.

EXAMPLES

[Example 1] MACS-Assisted Cell-SELEX

An experiment was performed to select a single stranded DNA aptamer that specifically binds to astrocytes. An aptamer that binds non-specifically to dead cells is one of the most significant drawbacks. Therefore, antibody sorting using MACS makes it possible to select only live astrocytes, which is different from existing cell SELEX.

(1) Experimental Materials

An astrocyte, which is a target cell, and a neuron, which is a counter cell, were prepared.

Thereafter, a DNA library was prepared (IDT, US), and each DNA has a 15 bp forward and reverse primer binding site at the 5' and 3' ends, respectively, and includes a 40mer random sequence in the middle.

The sequences are arranged as follows.

```
Sequence
5'-ATGCGGATCCCGCGC (NNNNNNNNNNNNNNNNNNNNNNNNNNNNNNNNNNNNNNNN)

CGCGCGAAGCTTGCG-3'

Forward primer:
5'-ATGCGGATCCCGCGC-3'

Reverse primer:
5'-CGCGCGAAGCTTGCG-3'
```

A binding buffer was prepared. The binding buffer includes 1 liter of Dulbecco's Phosphate-Buffered Saline (DPBS), 4.5 g of glucose, 100 mg of salmon sperm DNA, 1 g of BSA and 5 ml of 1 M $MgCl_2$. A washing buffer was prepared. The washing buffer includes 1 liter of DPBS, 4.5 g of glucose, and 5 ml of 1 M $MgCl_2$.

(2) Experimental Procedure

① Negative SELEX (Performed from Round 2)

Neurons were densely cultured on a 100 pi plate. Thereafter, the plate was washed twice with 10 mL of the binding buffer to remove the media. Floating cells were primarily collected in a test tube by adding 5 mL of Accutase thereto, and the cells were removed from the plate by adding 5 mL of DPBS thereto and using a cell scrapper, and cultured.

Centrifugation was performed at 300 g for 10 minutes, and the cells were resuspended with 350 ul of the binding buffer. The cells were mixed with a binding buffer containing an aptamer and cultured at 4° C. After centrifugation was performed at 300 g for 10 minutes, 450 ul of a supernatant was collected and used for positive SELEX.

② Positive SELEX

Astrocytes were prepared in the same manner as above, and resuspended in 500 uL of the binding buffer. A supernatant obtained from negative SELEX was combined with the cells, and the resulting mixture was incubated at 4° C. The mixture was centrifuged at 300 g for 10 minutes, and washed three times with 1 ml of the washing buffer, and only live astrocytes were selected by performing sorting with MACS as anti-GLAST. This procedure was added from Round 14.

③ Elution

The supernatant was discarded by centrifuging cells obtained by performing sorting with MACS at 300 g for 10 minutes, and was resuspended in 500 ul of distilled water. After the suspension was boiled at 95° C. for 10 minutes and centrifuged at 13100 g for 5 minutes, only the supernatant was taken. An aptamer library was amplified by PCR and used in the next round.

④ Selecting Pressure

The amount of aptamer library was reduced step-by-step from 4 nmol to 35 pmol. A binding time with a target cell decreased from 1 hour to 10 minutes. A binding time with a counter cell increased to 1 hour starting from 0 minutes at Round 1 and 30 minutes at Round 2.

In this case, MACS was added from Round 14.

The following experiment was performed to amplify and prepare a single stranded DNA library used in the next round.

⑤ Sequential Linear PCR 23 ul of an eluate, 25 ul of 2× Go Taq (Promega, US), 1 ul of a 25 uM forward primer, and 1 ul of a 25 uM reverse primer were mixed, and the mixing was performed five times. Using a PCR product obtained from the above procedure as a template, 5 ul of the template, 25 ul of 2× Go Taq, 1 ul of a 25 uM forward primer, 1 ul of a 25 uM reverse primer, and 18 ul of DW was mixed, and the mixing was performed five times, ten times, and fifteen times.

Amplification was confirmed by running the mixture on a 3% agarose gel, and 8 sequential linear PCR runs were performed under a condition in which only a desired 70 bp ds-DNA was present. A dsDNA was prepared by running the mixture on a 3% agarose gel to extract the gel.

⑥ Asymmetric PCR

Asymmetric PCR was performed using the dsDNA prepared in ① as a template. 1 ul of the template, 25 ul of 2× Go Taq, 1 ul of a 25 uM forward primer, 1 ul of a 2.5 uM reverse primer, and 22 ul of DW were mixed, and the mixing was performed fifteen times, twenty times, and twenty five times. After confirmation on the agarose gel, 24 PCR run were performed under a condition in which 70 bp ssDNA was amplified the most.

The gel was eluted with 240 ul of nuclease free-water by performing gel extraction.

⑦ Concentration and Buffer Change

Centrifugation was performed at 14000 g for 10 minutes with a 10 K Amicon filter. 400 ul of 1×DPBS was added thereto, and the centrifugation process was repeated. Only a sample on the filter was taken.

⑧ Refolding Before Use

A process of refolding an aptamer including all SELEX rounds and an aptamer library or a selected aptamer prior to target binding was performed. The sample was boiled at 95° C. for 10 minutes, and then rapidly cooled on ice for 10 minutes.

[Example 2] RT-qPCR for Confirming Binding to Aptamer

An experiment was performed to confirm whether the aptamer was attached well to the surface of target astrocytes and whether Cell-SELEX was properly performed. Cells were prepared and washed twice with a washing buffer. A volume of 200 ul was finally incubated at 4° C. for 30 minutes such that 100,000 cells and 150 ng of aptamer were put into one sample. The sample was centrifuged at 300 g for 10 minutes and washed twice. The sample was resuspended with 200 ul of distilled water, and 1 or 2 ul was collected and used as a template. For qPCR, a total of 25 ul was prepared, and Cq values were analyzed by mixing 12.5 ul of 2×SYBR Taq, 1 ul of a 25 uM forward primer, 1 ul of a 25 uM reverse primer, a template, and DW, and then repeating 20 cycles. 2^-Cq was calculated and compared.

Figure 2:
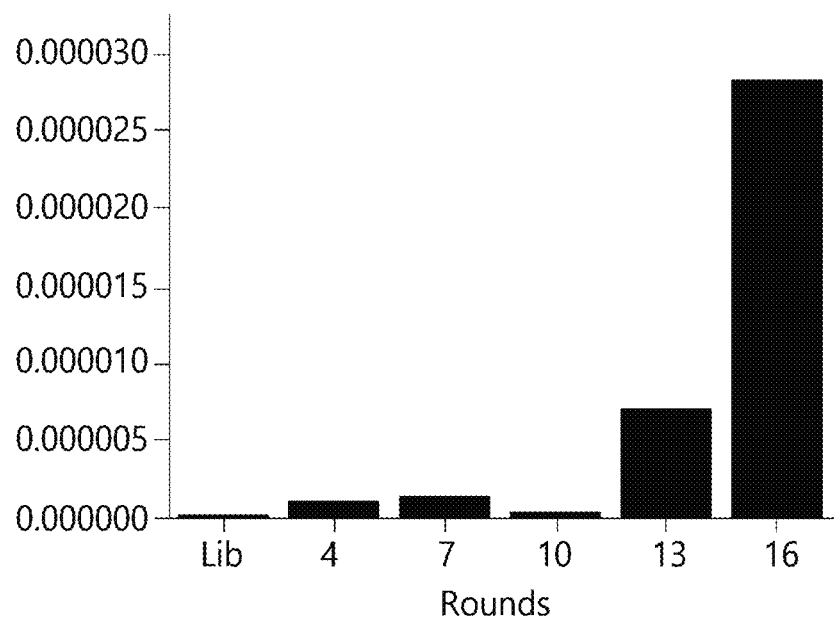
FIG. 2 illustrates the results of real-time quantitative PCR (RT-qPCR) for confirming whether an aptamer binds in a Cell-SELEX process according to an exemplary embodiment, and specifically illustrates that the inclusion of MACS after Round 13 increases binding affinity by a greater extent than before.
Figure 3:
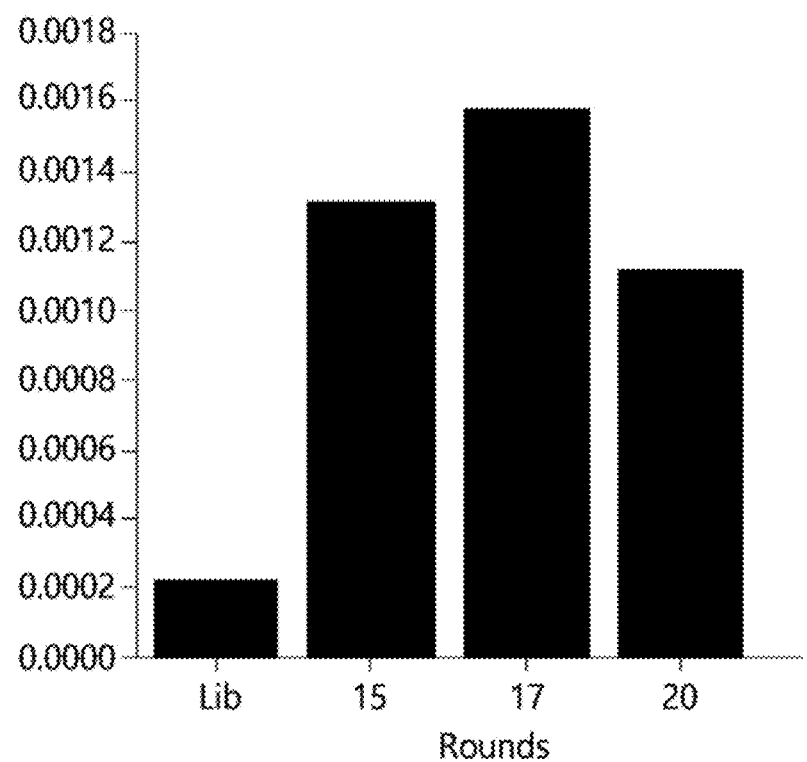
FIG. 3 illustrates the results of real-time quantitative PCR (RT-qPCR) for confirming whether an aptamer binds in a Cell-SELEX process according to an exemplary embodiment, and illustrates the highest binding affinity at Round 17.
Figure 4:
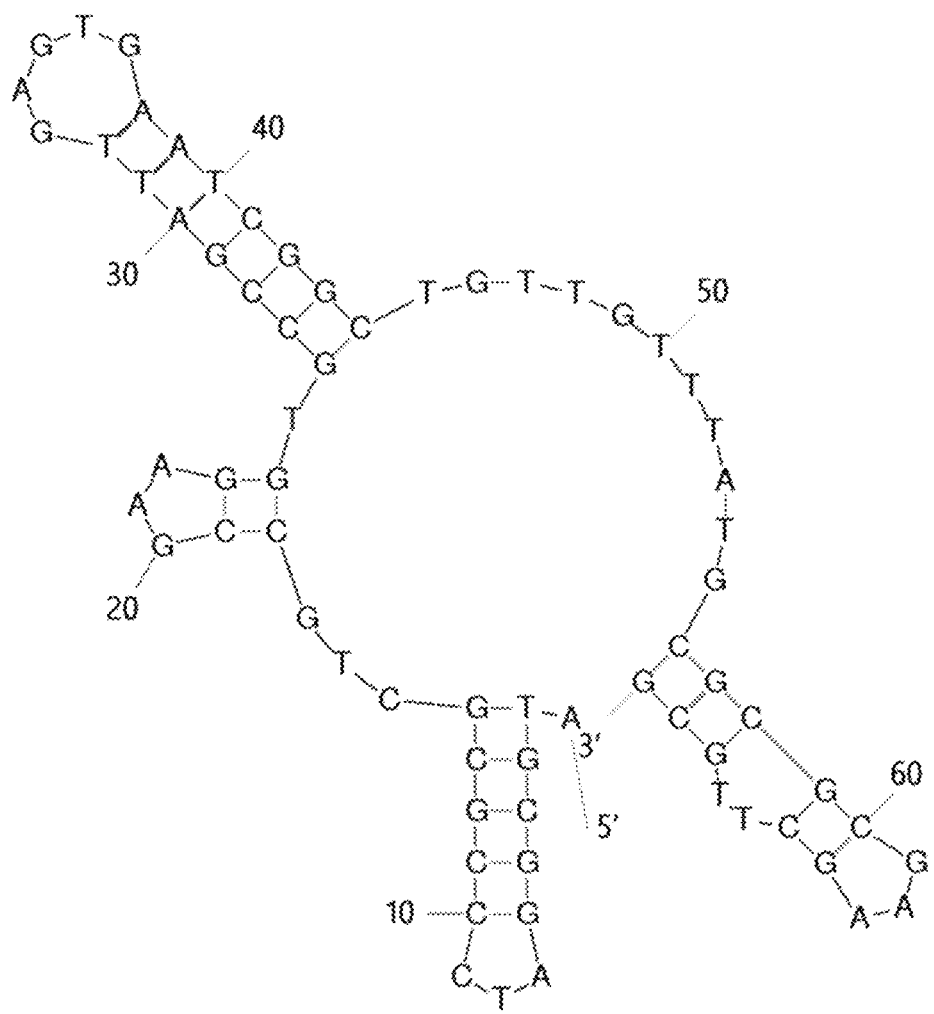
FIGS. 4 to 6 schematically illustrate a structure in which an aptamer candidate group and a primer are linked according to an exemplary embodiment.
Figure 5:
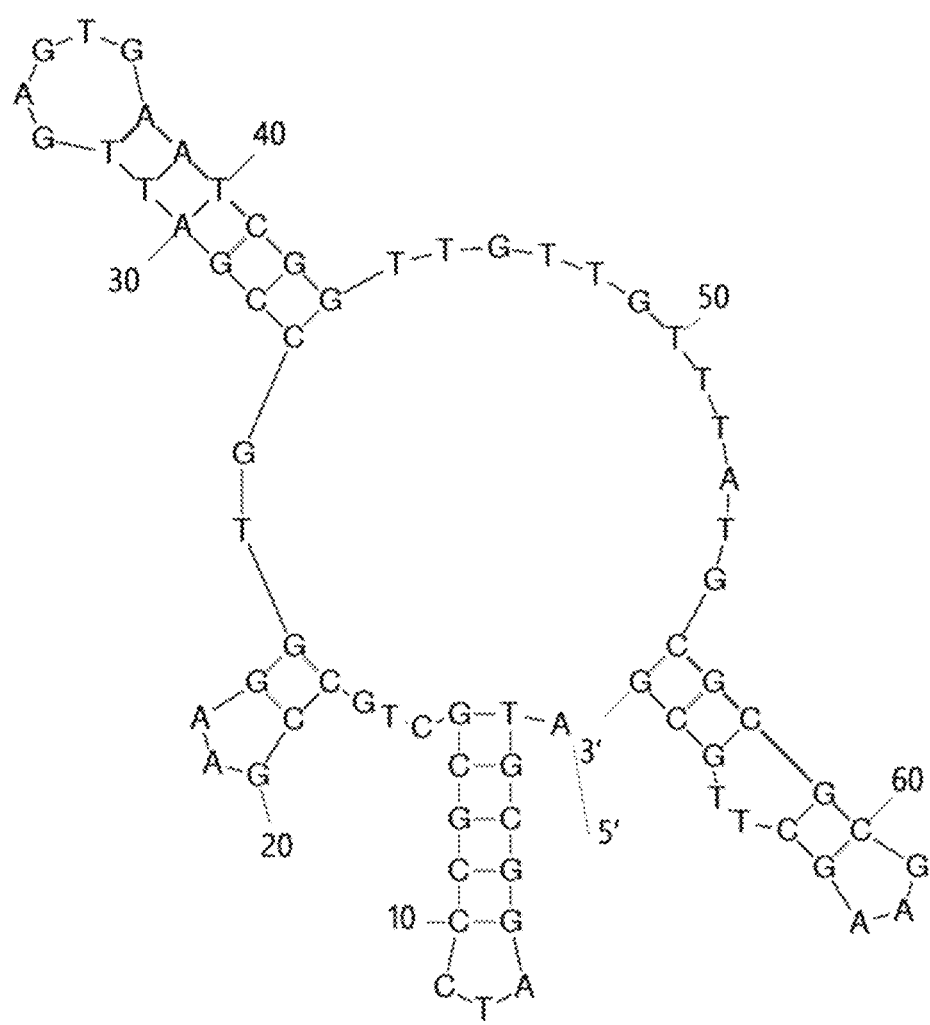
Figure 6:
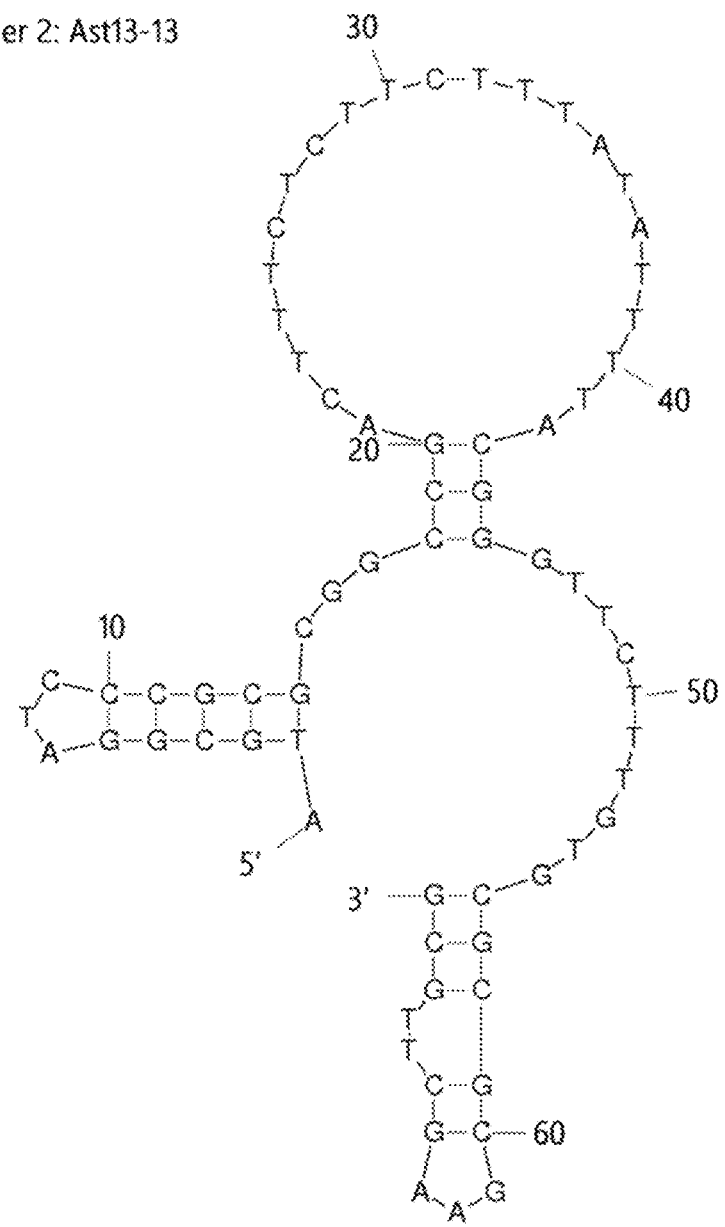
Figure 7:
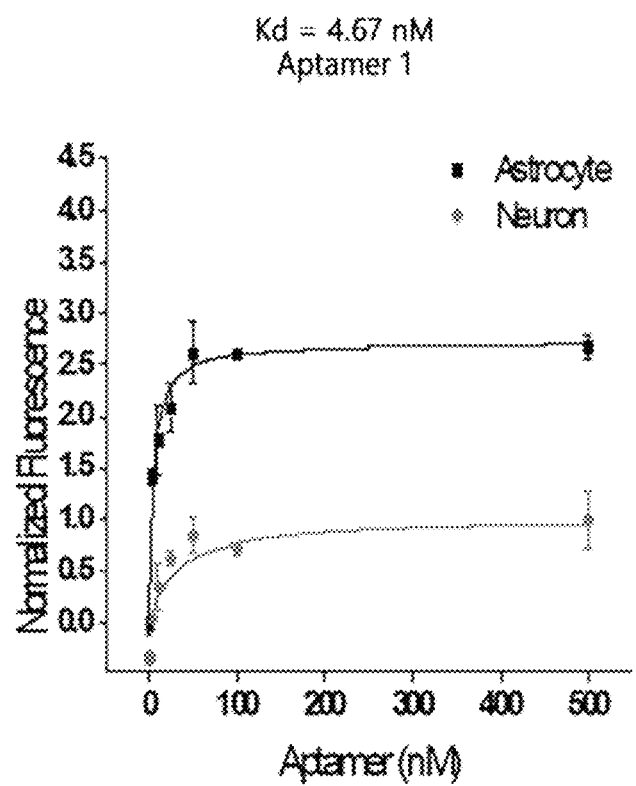
FIGS. 7 and 8 illustrates the results of verifying the astrocyte binding force of an aptamer candidate group according to an exemplary embodiment.
Figure 8:
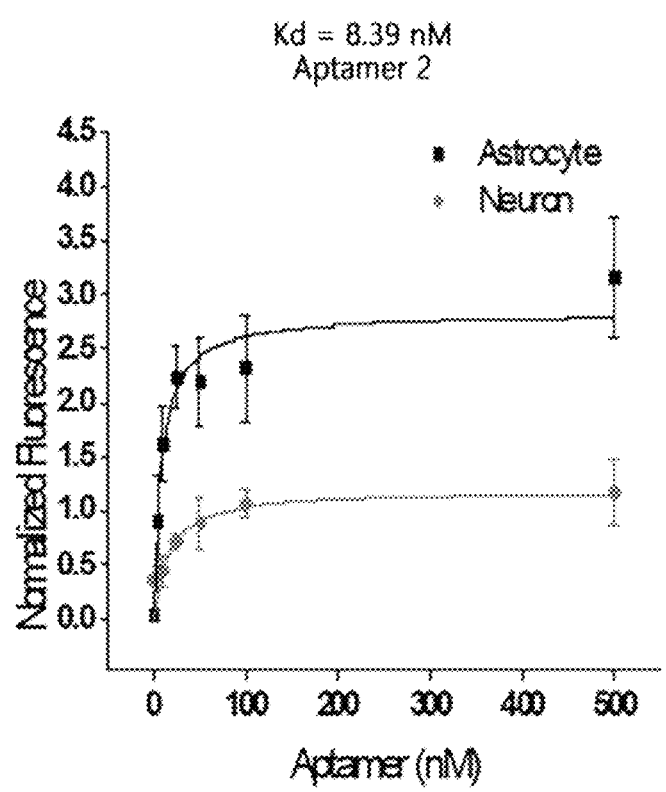
Figure 9:
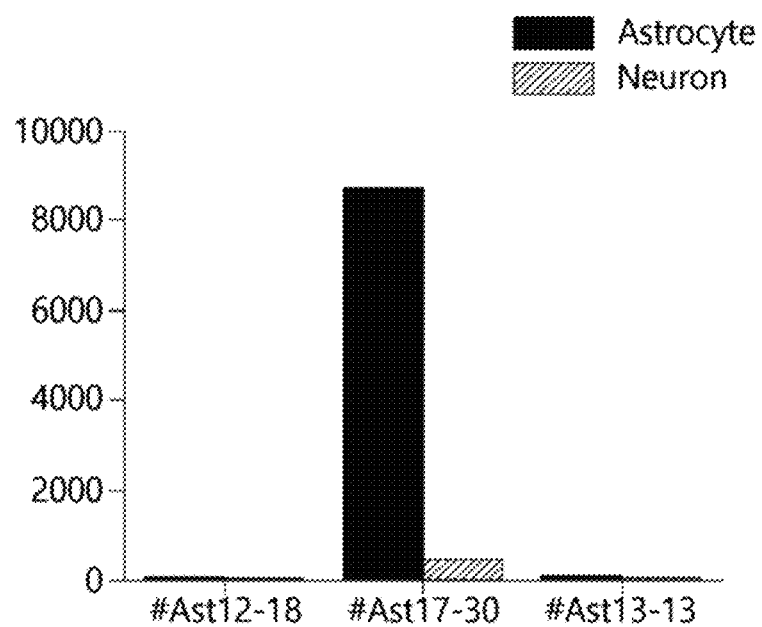
FIG. 9 illustrates the results of verifying a binding force to the astrocyte and neuron of an aptamer candidate group according to an exemplary embodiment through RT-PCT.
Figure 10:
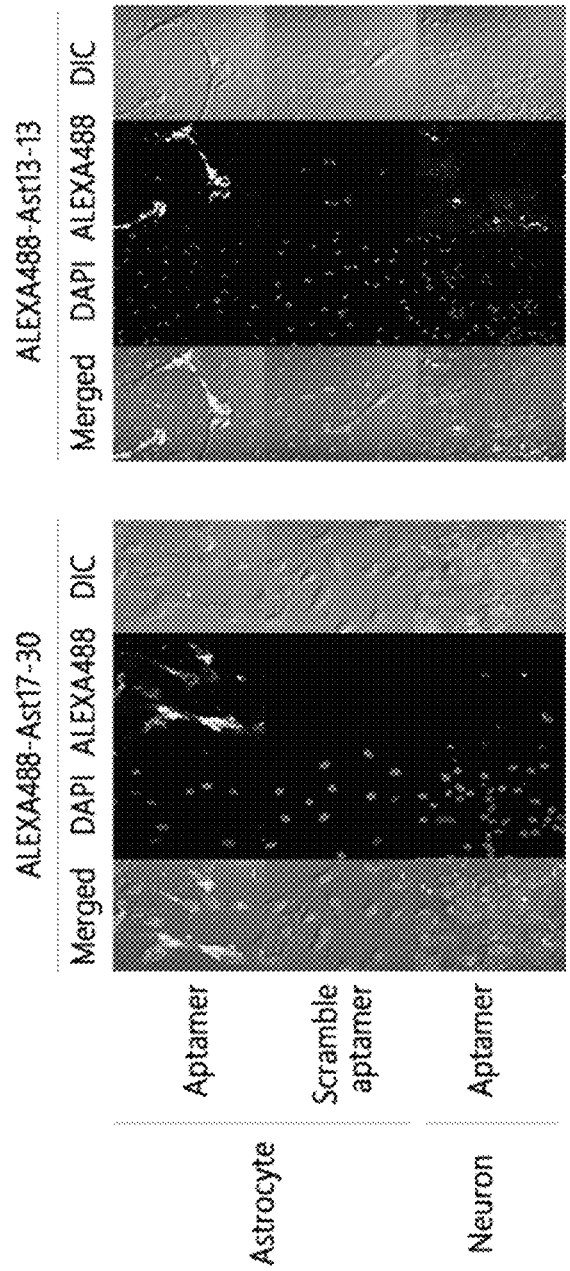
FIG. 10 illustrates astrocyte images using an aptamer candidate group according to an exemplary embodiment.
Figure 11:
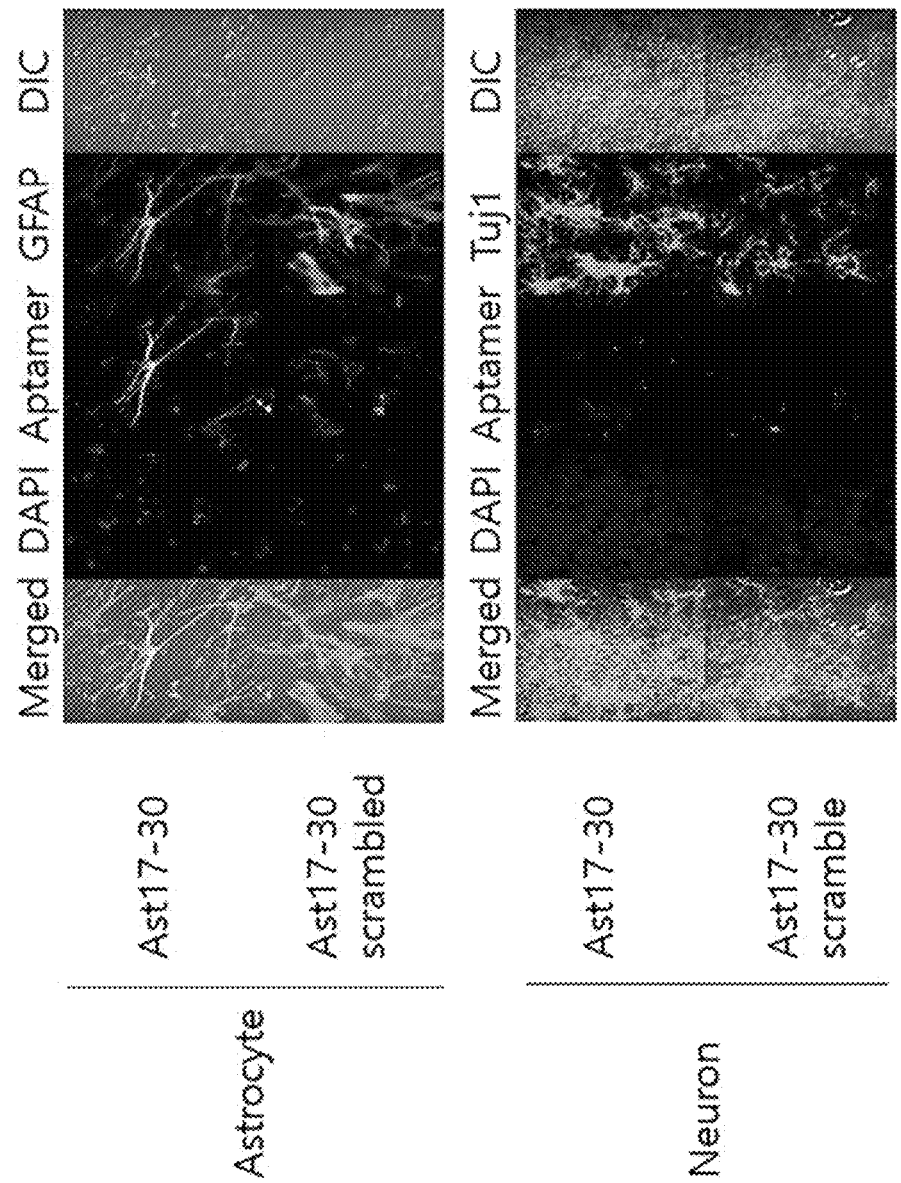
FIG. 11 compares astrocyte images using an aptamer candidate group according to an exemplary embodiment with the results of staining using an anti-GFAP antibody, and is intended to confirm whether signals of a known astrocyte marker and an aptamer are emitted from the same cell.
Figure 12:
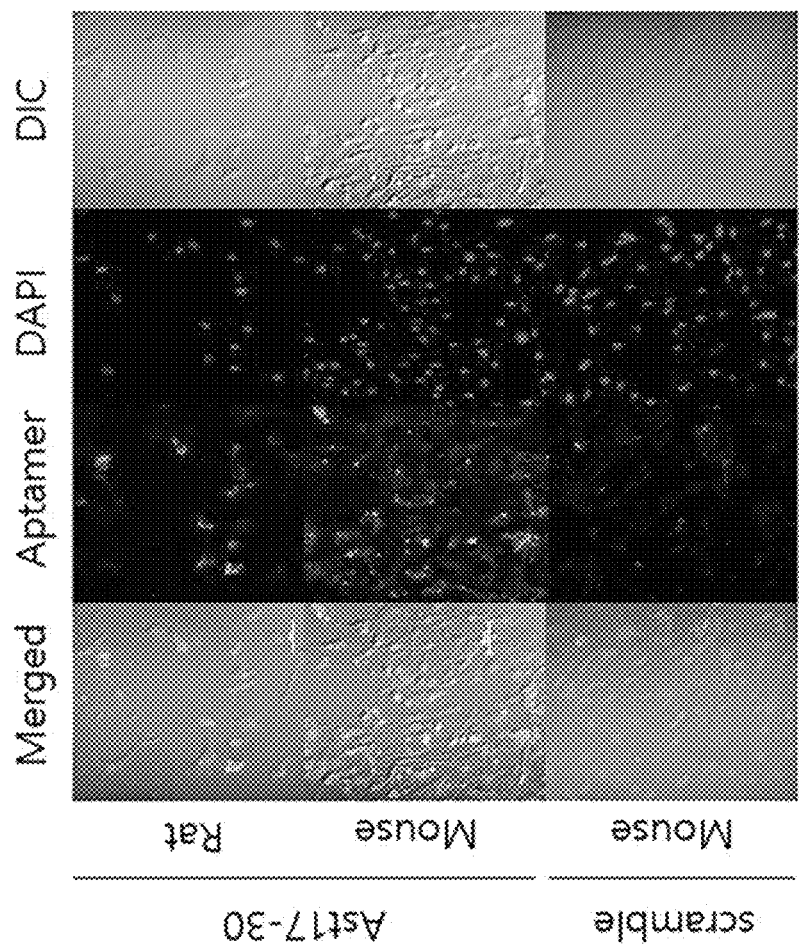
FIGS. 12 and 13 illustrate the results of confirming whether an aptamer candidate group according to an exemplary embodiment has species specificity.

As a result, MACS was not included until Round 13, but the amount of aptamer binding to astrocytes increased compared to the library, and after Round 14 in which MACS was combined, the amount of aptamer binding was significantly increased to a greater extent than before (Round 16)(FIG. 2).

When only the rounds including MACS (Rounds 14 to 20, wherein, only Rounds 15, 17, and 20 were measured) were compared, the highest amount of aptamer binding was shown at Round 17. Since the amount decreased at Round 20, it was judged that the aptamers bound at the previous rounds were likely to be selectively saturated, and the aptamer pool bound at Round 17 was finally sequenced.

[Example 3] Identification of Aptamers Specifically Bound to Astrocytes Through Sequencing As a result of monitoring, sequencing was performed to search for an aptamer candidate from the products of the round with the best binding affinity. Sequencing was performed at Round 13 (including no MACS) and Round 17 (including MACS), respectively.

(1) Experimental Materials

A T-vector cloning vector, a ligase, competent cells, double stranded DNA, LB media, and a mini prep kit were prepared.

(2) Experimental Method

The final rounds 12 and 13 before the introduction of MACS and the best round, round 17, after the introduction of MACS were sequenced.

① TA Cloning

DsDNA was prepared by performing linear PCR using a Taq polymerase. The T-Vector and the dsDNA were attached (ligation) and stored at 4° C. Competent cells were transformed and cultured on a 37° C. antibiotic LB plate.

② Plasmid-Miniprep for Sequencing

A single colony was taken by a sterilized pipette tip and cultured in 5 mL of LB media at 37° C. A plasmid was miniprepared for preparation from all pellets by performing centrifugation at 4000 g for 5 minutes. Sequencing was performed by elution in 50 ul of distilled water. A total of 100 colonies were sequenced and multi-aligned, and candidates were selected in the order of high frequency of appearance and then stability (low free energy).

[Example 4] Finally Excavated Aptamer Candidate Group

The secondary structure of the aptamer was analyzed by an mfold web server (M. Zuker. Mfold web server for nucleic acid folding and hybridization prediction. NucleicAcidsRes. 31 (13), 3415, 2003), and the secondary folding structure of all 70 mers including primers were confirmed. The sequences of Aptamers 1-1, 1-2 and 2 were represented by SEQ ID Nos: 1 to 3 in the direction of 5' to 3', and it was confirmed that the difference between Aptamers 1-1 and 1-2 is a difference in one base.

The scramble aptamers, which are the negative controls of each Aptamer 1 and 2, were represented by SEQ ID Nos: 11 and 12.

TABLE 2

| No. | Aptamer | Sequence in direction of 5'to 3' (in order of primer (15mer)-aptamer (40mer)-primer (15mer)) |
|---|---|---|
| 1 | 1-1 | ATG CGG ATC CCG CGC TGC CGA AGG TGC CGA TTG AGT GAA TCG GCT GTT GTT TAT GCG CGC GAA GCT TGC G |
| 2 | 1-2 | ATG CGG ATC CCG CGC TGC CGA AGG TGC CGA TTG AGT GAA TCG GTT GTT GTT TAT GCG CGC GAA GCT TGC G |
| 3 | 2 | ATG CGG ATC CCG CGC GGC CGA CTT TCT CTT CTT TAT ATT TTA CGG GTT CTT TGT GCG CGC GAA GCT TGC G |
| 4 | Scramble 1 | ATG CGG ATC CCG CGC GTA GTT GTG GTG GCT ACG CAT CGT ATC TGG TGA TCA GTG ACG CGC GAA GCT TGC G |
| 5 | Scramble 2 | ATG CGG ATC CCG CGC TTC GGT ATT TTT ATT CTT TTC CCT GTT AGG CTA GTC CTG GCG CGC GAA GCT TGC G |

The sequences of the finally excavated aptamer candidates are summarized in the table as follows.

The following aptamers include 15mer primers at the 5' end and 3' end, respectively.

[Example 5] Assay of Binding Force to Astrocytes Using Aptamer Candidates

The following experiment was performed to confirm the binding affinity of aptamer candidates.

The method was the same as the preparation method for monitoring, but 2 ul of a template was put into a final volume of 12.5 ul, and the process was repeated twenty times. In this case, the experiment was performed with Aptamer 1-2 as Aptamer 1. The number of astrocytes and the number of neurons (about 100,000) were equally used, the concentration of each aptamer was added differently within a range of 0 to 500 nM, and then the amount of aptamer binding to the final cells through the washing process was analyzed by RT-qPCR.

All aptamer candidate groups used were non-labeled full length aptamers and synthesized by IDT. The end point fluorescence signal of SYBR green used in RT-qPCR was normalized and plotted using the Michaelis-Menten formula. Both experiments were repeated in triplicate to obtain an average value.

As a result, it was confirmed that Aptamer 1-1 and Aptamer 2 had binding affinity for astrocytes, and Aptamer 1-1 had higher binding affinity and specificity for astrocytes than Aptamer 2.

[Example 6] Astrocyte Imaging Using Excavated Astrocyte Aptamer

The excavated astrocyte aptamer was used until 13-13, and the astrocyte images were compared. The method of Example 11-1 was used for staining the aptamer.

As a result, it was confirmed that the part where the aptamer signal appeared was not a neuron but an astrocyte.

[Example 7] Comparison of Astrocyte-Aptamer Imaging and GFAP Antibody Staining

The following experiment was performed to confirm whether known astrocyte marker and aptamer signals came from the same cell.

As a result, it was confirmed that the part where the aptamer signal appeared and the part where the signal of GFAP, which is an astrocyte marker, appeared matched.

In the case of the scramble aptamer, almost no aptamer signal was observed compared to Ast 17-30.

[Example 8] Confirmation of Aptamer Species Specificity (Comparison of Binding to Rat and Mouse Astrocytes)

250 nM ALEXA488-Ast17-30 was used for imaging.

In the case of FACS, the cells were removed and bound to 0, 125 nM, 250 nM, and 500 nM ALEXA488-Ast17-30 and imaged for confirmation.

As a result of observing under a 400× confocal microscope, it was observed that aptamers were attached to mouse and rat astrocytes at a similar level.

[Example 9] Preparation of Aptamer Trimer

Ast17-30, which is one of the aptamers, has a full length of 70 mer. A truncated aptamer (t-aptamer) was manufactured by cutting out the remaining part excluding an effective part among the full length (tAst17-30).

Figure 13:
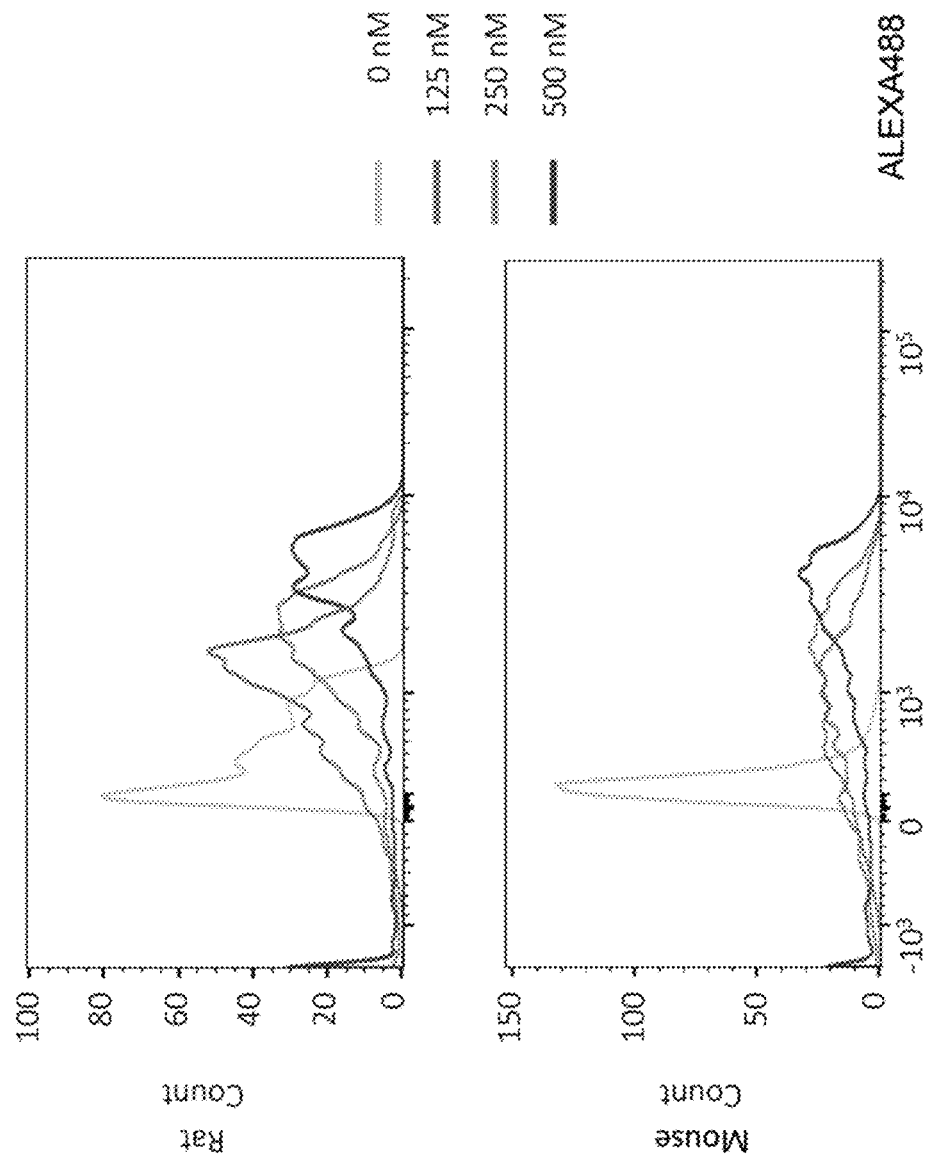
Figure 14:
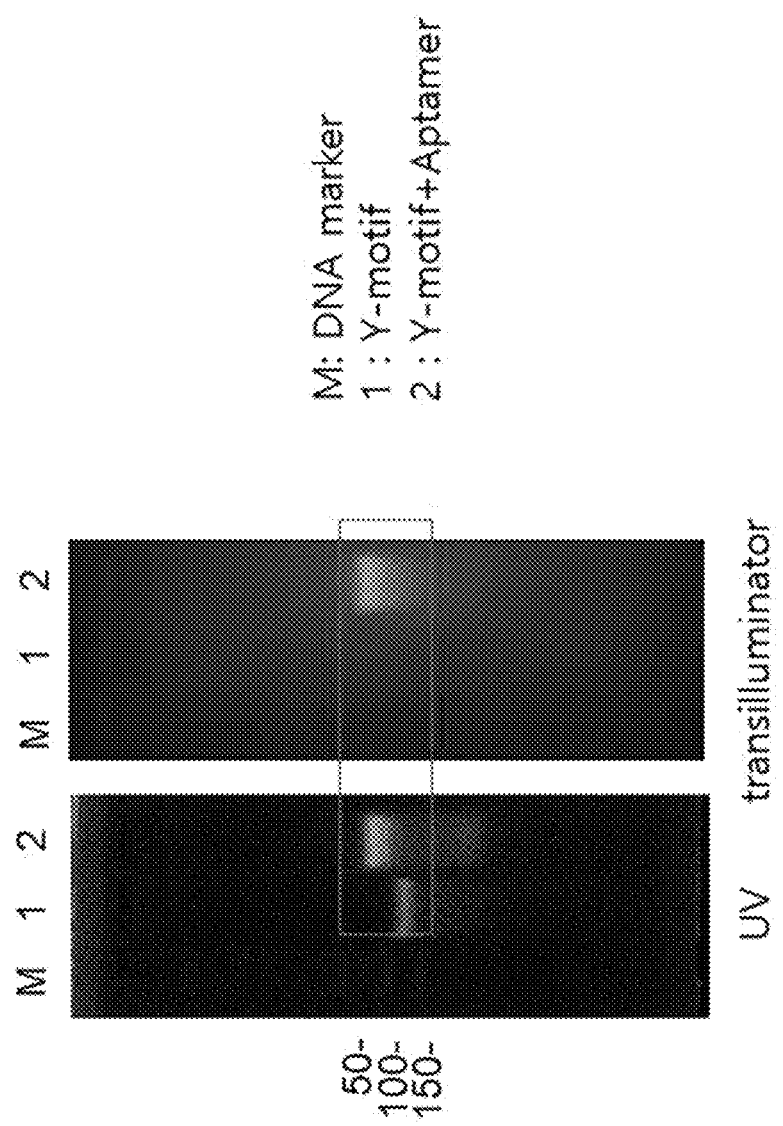
FIGS. 14 and 15 illustrate data on a process of preparing an aptamer trimer according to an exemplary embodiment and synthesis results.
Figure 15:
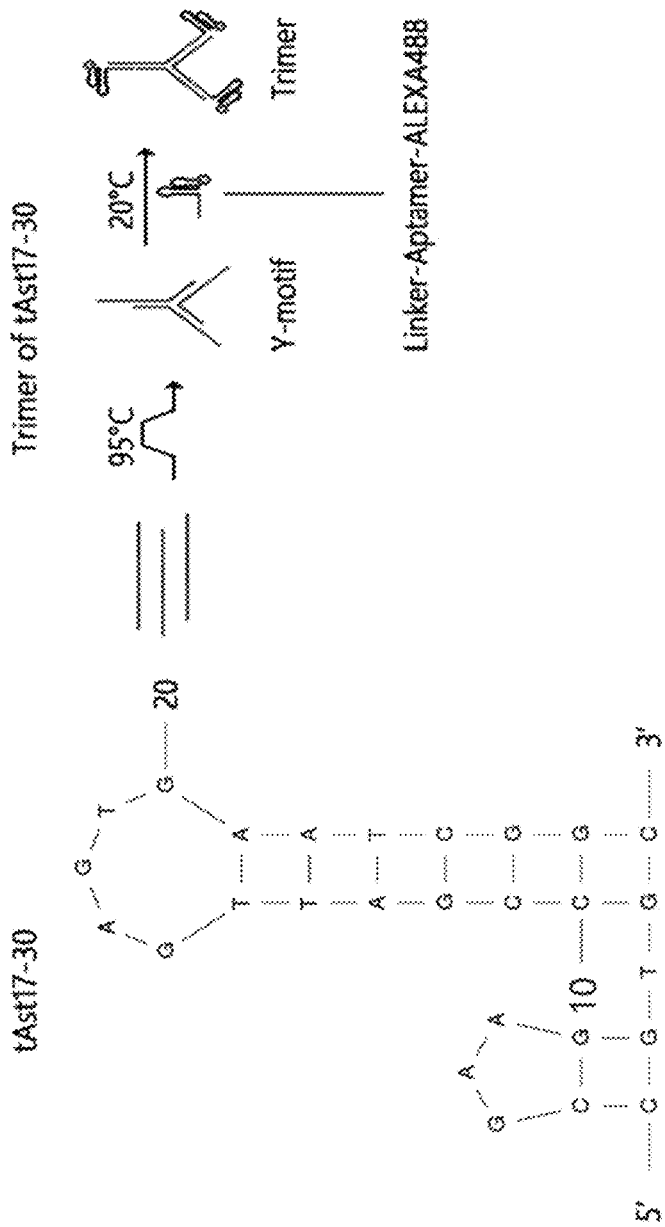

A trimer was prepared. In order to construct a Y-shaped motif, single stranded DNA having a complementary sequence as in FIG. 13 was synthesized. The single stranded DNA was boiled at 95° C. for 2 minutes and cooled to 4° C. at a rate of 1° C./min. A 3-fold higher mole number was put thereinto than the Y motif containing tAst17-30 in which a linker was attached to the 5' position and a fluorescent material was attached to the 3' position. The mixture was allowed to react at 20° C. for 1 hour. It was confirmed that it was properly synthesized on a 3% agarose gel. The trimer prepared by the process was used as it was in the experiment without further purification.

Figure 16:
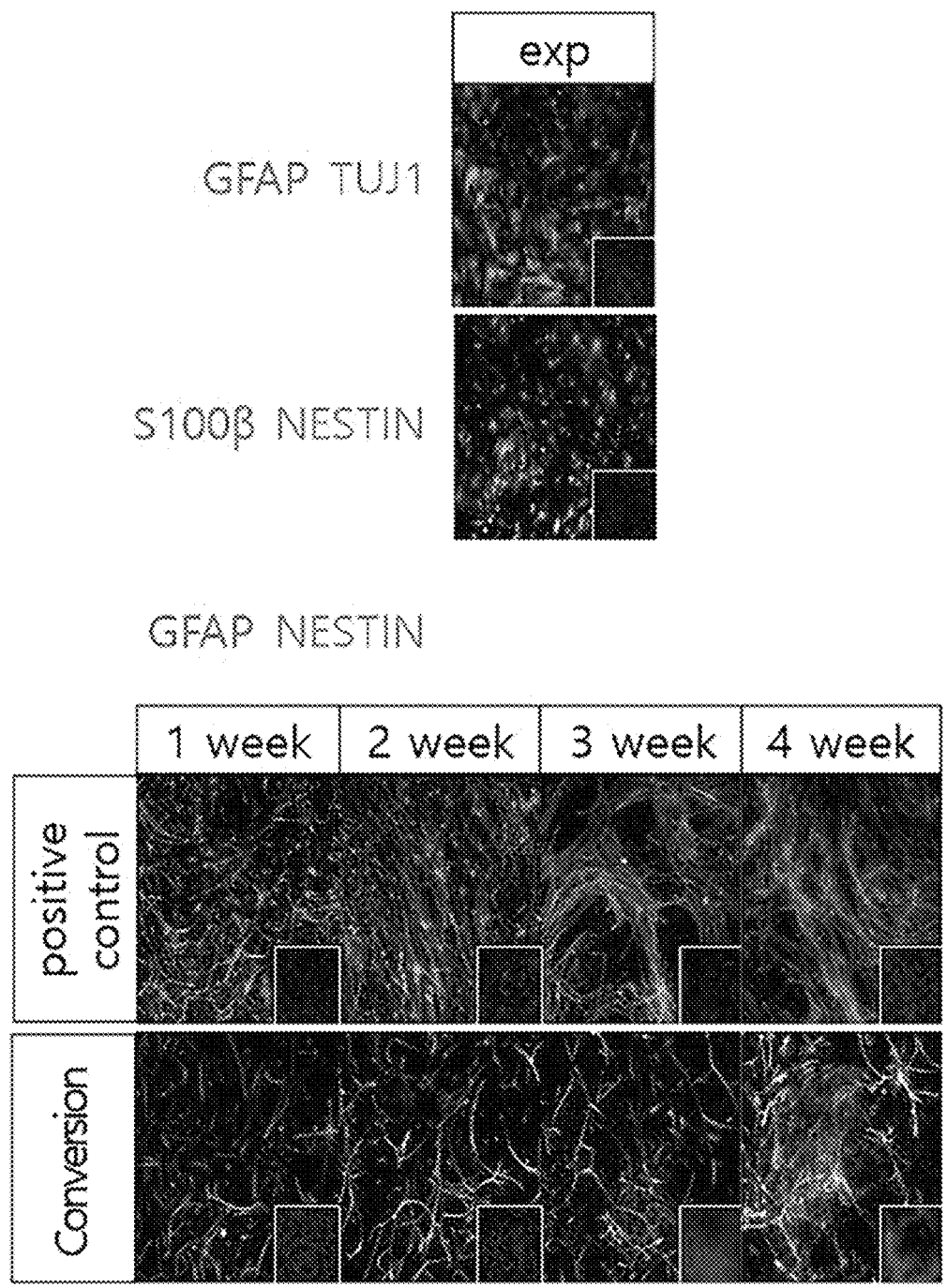
FIG. 16 illustrates data confirming that the differentiation of primary astrocytes can be monitored using an astrocyte-specific binding force of the aptamer selected to monitor a conversion process performed for 5 weeks using an aptamer according to an exemplary embodiment.
Figure 17:
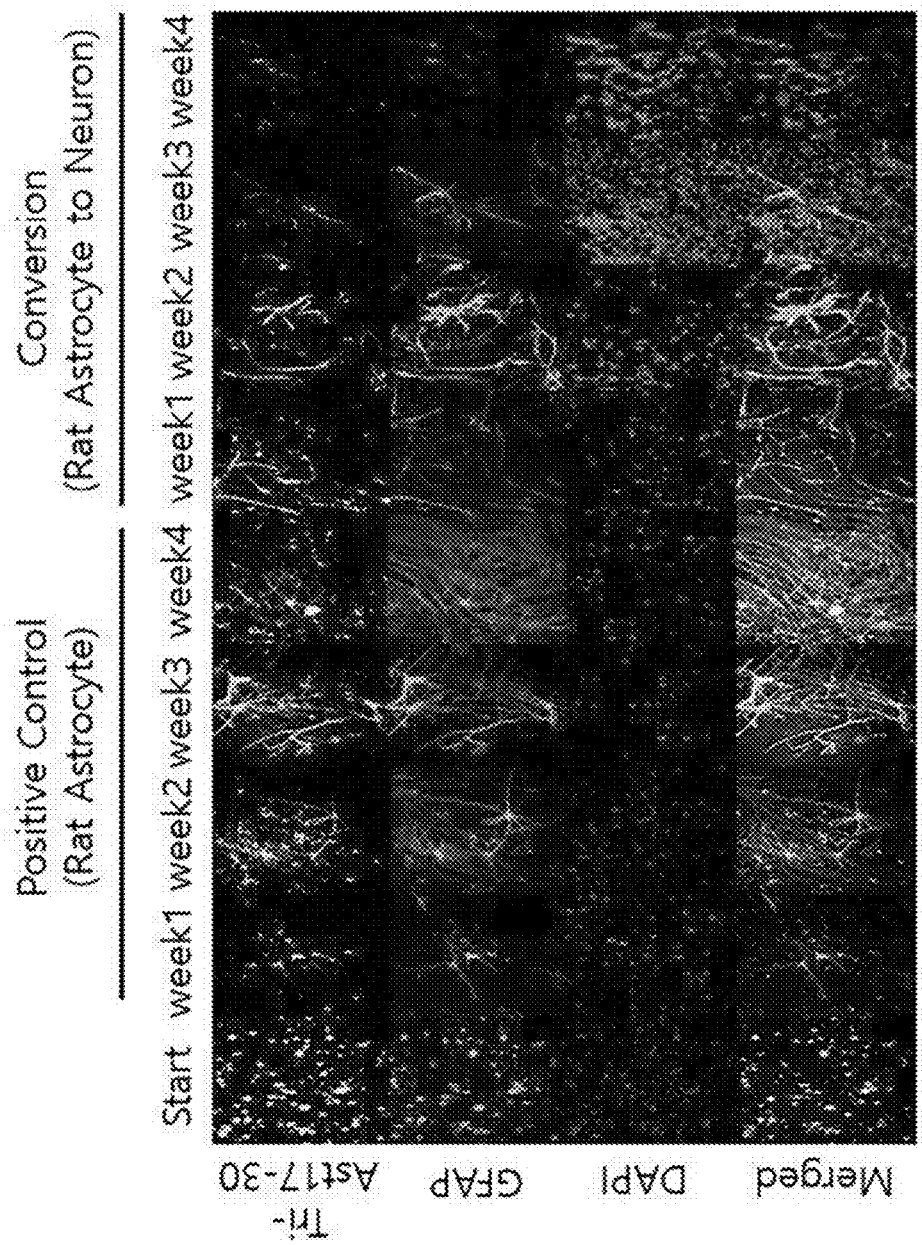
FIGS. 17 to 19 are the results of monitoring a conversion process using a trimer according to an exemplary embodiment.
Figure 18:
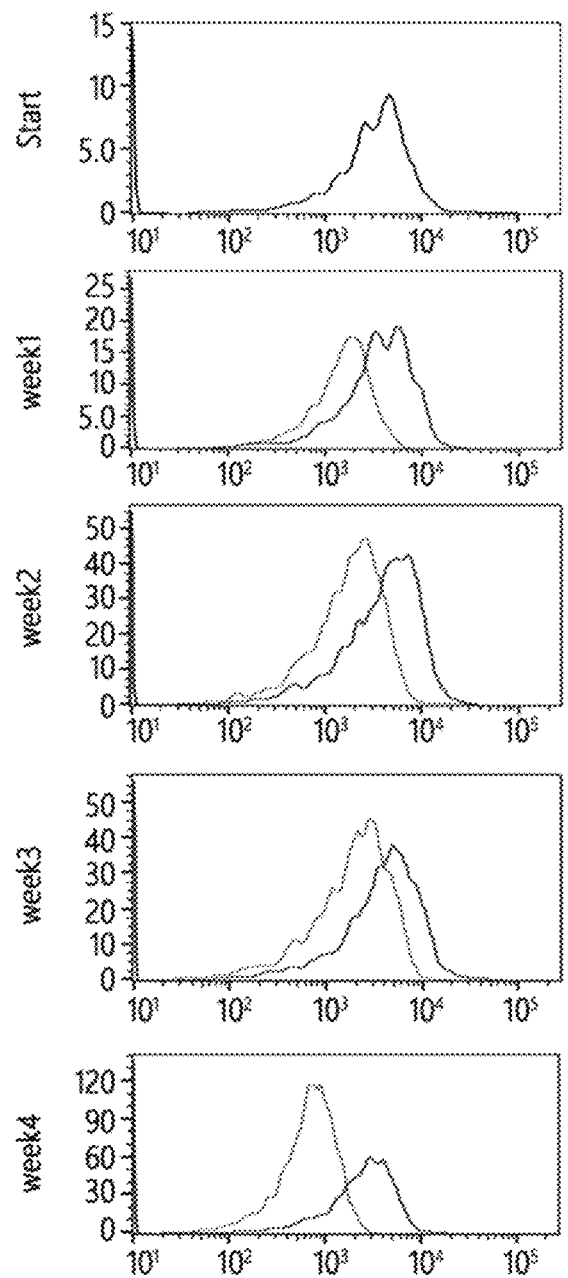
Figure 19:
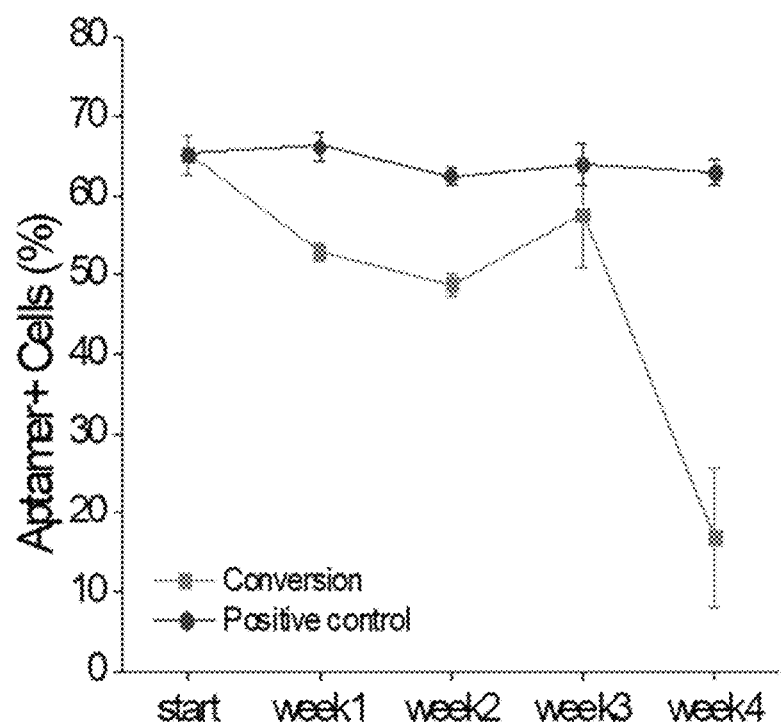
Figure 20:
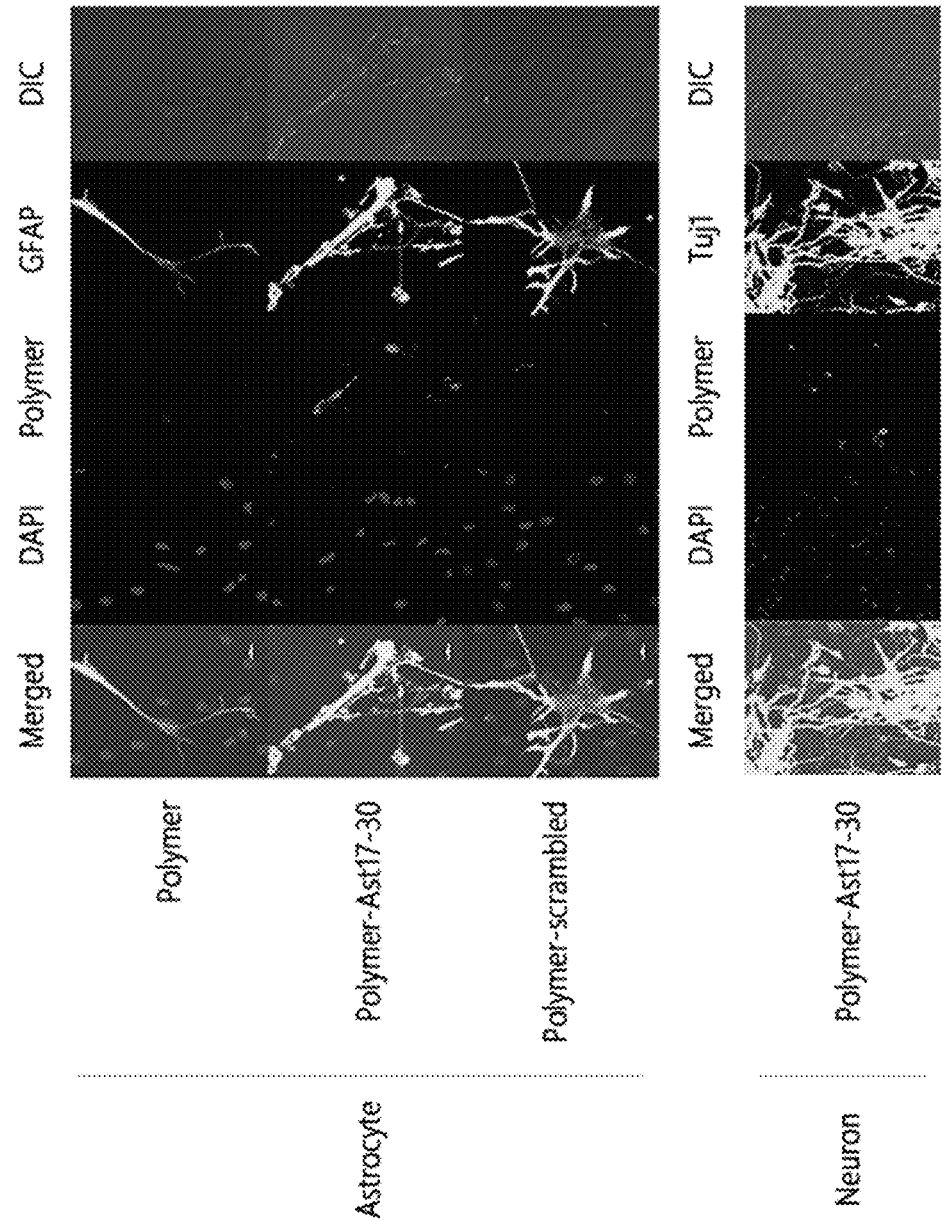
FIG. 20 is a result confirming whether a polymer coated with an astrocyte aptamer according to an exemplary embodiment is specifically internalized to astrocytes.

[Example 10] Rat Astrocyte to Neuron Precursor Cell Conversion Monitoring Using Trimer A conversion process was monitored for 5 weeks. Expanded cells corresponded to week 1, and thereafter, conversion was performed for 4 weeks (FIG. 16). Astrocytes were stained with GFAP and neural precursor cells were stained with NESTIN for monitoring. A positive control group is an astrocyte sample of rats, and a conversion sample is a sample in which differentiation is in progress.

Conversion was monitored using a 250 nM trimer. Conversion was monitored by FACS using a trimer to which 250 nM ALEXA488 was attached. As a result, the differentiation of primary astrocytes was monitored using the astrocyte-specific binding force of the selected aptamer.

[Example 11] Other Experiments

Example 11-1. Aptamer Staining (1) Experimental Preparation

An ALEXA488-aptamer, an aptamer binding buffer, 6 uM dextran sulfate ($DxSO_4$), and an aptamer washing buffer were prepared for aptamer binding. As the buffer, the same buffer as the buffer during the SELEX preparation process was used.

The binding buffer was prepared by boiling salmon sperm DNA, which is a blocking agent, at 95° C. for 15 minutes to denature the salmon sperm DNA and cooling the same on ice for 15 minutes.

For the aptamer preparation, an aptamer was boiled at 95° C. for 5 minutes, gradually cooled to room temperature (15 minutes), and refolded.

The cells were prepared by putting a cover glass on a 24-well plate and growing them to fill the same.

(2) Experimental Procedure

First, the media was removed by washing the media twice with 1 ml of the washing buffer. 500 ul of a binding buffer including DxSO4 was added, and the resulting mixture was blocked at 37° C. for 10 minutes. The blocking solution was removed, an aptamer was prepared in a solution including 200 ul of a binding buffer including DxSO4, and cells were treated with the aptamer, and then cultured at 37° C. for 1 hour in a dark room to bind the aptamer to the cells. The cells were washed three times with 500 ul of the washing buffer for 3 minutes each. The cells were stored in a 4% formaldehyde solution in a dark room at room temperature for 10 minutes. The cells were washed three times with 500 ul of DPBS for 5 minutes each. A drop of DAPI and a mounting medium was dropped on a slide glass, and the slide glass was covered by a cover glass to remove the media adhering to the surroundings. The area around the cover glass was fixed with a transparent nail polish and stored in a dark room at 4° C. until the time for confocal observation.

Example 11-2. IHC (1) Experimental Preparation

A primary antibody (anti-GFAP, anti-Tuj1), a fluorophore-labeled secondary antibody, a primary antibody blocking buffer (10% normal goat serum (NGS) and 0.3% Triton-X 100 (TX100) in 0.1% BSA/PBS), a primary antibody binding buffer (10% NGS in 0.1% BSA/PBS), a secondary binding buffer (0.1% BSA/PBS), a washing buffer (0.1% BSA/PBS), and a fixative solution (4% formaldehyde in DPBS) were prepared.

(2) Experimental Method

① after Aptamer Treatment, the Following Process was Performed after Fixation.

1st Ab Binding

About 300 μL of 0.1% BSAPBS was sprayed on the side of a plate wall, incubated for 5 minutes, and then washed three times. 0.1% BSAPBS was treated with 300 μL of a mixture obtained by mixing 10% normal goat serum (NGS)

and 0.3% Triton-X100 (TX100), and then blocked at room temperature for 1 hour. 0.1% BSA/PBS was treated with 200 μL of a mixture obtained by mixing 10% NGS and a primary Ab (1/2000), and then stored at 4° C. In this case, anti-GFAP was used for anti-astrocyte, and anti-Tuj1 was used for anti-neuron.

2nd Ab Binding

About 300 μL of 0.1% BSA/PBS was sprayed on the side of a plate wall, incubated for 5 minutes, and then washed three times. 0.1% BSA/PBS was mixed of a secondary Ab (1/500) and treated with 200 μL, and then stored in a dark room at room temperature for 1 hour. About 300 μL of 0.1% BSA/PBS was sprayed on the side of a plate wall, incubated for 5 minutes, and then washed twice, and then washed twice with PBS. A drop of a mounting medium including DAPI was dropped on a slide glass, the slide glass was covered by a cover glass, and the mounting medium adhering to the surroundings was removed. The area around the cover glass was fixed with a transparent nail polish and stored in a dark room at 4° C. until the time for confocal observation.

Although embodiments have been described with limited embodiments and drawings as described above, those skilled in the art can make modifications and variations from the above description. For example, even though the techniques described may be performed in a different order than the methods described, or replaced or substituted by other components or equivalents, appropriate results can be achieved.

```
Sequence List_Free Text
Aptamer 1-1:
                                       (SEQ ID NOs: 1)
TGCCGAAGGTGCCGATTGAGTGAATCGGCTGTTGTTTATG Aptamer 1-2:
                                       (SEQ ID NOs: 2)
TGCCGAAGGTGCCGATTGAGTGAATCGGTTGTTGTTTATG Aptamer 2:
                                       (SEQ ID NOs: 3)
GGCCGACTTTCTCTTCTTTATATTTTACGGGTTCTTTGTG Aptamer 3:
                                       (SEQ ID NOs: 4)
GGCCGACTTTCTTTTTTTCATGTCTTACGGGTTCTTTGTG Aptamer 4:
                                       (SEQ ID NOs: 5)
GGCCGGCTTTTTCTTTTCTTTATATTTTATGGGTTCTCTGTG Aptamer 5:
                                       (SEQ ID NOs: 6)
GGCCGACTTTTTTTTTTTTATATTTTACGGGTCCTCTGTG Aptamer 6:
                                       (SEQ ID NOs: 7)
GGCCGACTTTTTTTTTTTATATTTTACGGGTCCTCTGTG Aptamer 7:
                                       (SEQ ID NOs: 8)
GGCCAATCTTTTTTTTTATATTTTACGGGTCCTTTGTG Aptamer 8:
                                       (SEQ ID NOs: 9)
GGCCAACTTTTTCTTTTTATATTTACGGGTCTTCTGTG Aptamer 9:
                                       (SEQ ID NOs: 10)
GGCCGACTTTTTCTTTCTTATATTTTACGTGTTTTTGTG Scramble aptamer 1:
                                       (SEQ ID NOs: 11)
GTAGTTGTGGTGGCTACGCATCGTATCTGGTGATCAGTGA Scramble aptamer 2:
                                       (SEQ ID NOs: 12)
TTCGGTATTTTATTCTTTTCCCTGTTAGGCTAGTCCTGG
```

The invention claimed is:

1. An aptamer capable of binding an astrocyte,
wherein the aptamer is a single strand,
wherein the aptamer consists of 80 or less nucleotides, and
wherein the aptamer comprises a polynucleotide sequence of any one of SEQ ID NOs: 1 to 10, or a fully complementary polynucleotide sequence thereof.

2. The aptamer of claim 1,
wherein the aptamer further comprises a primer sequence in a first terminal or a second terminal of the polynucleotide sequence of any one of the SEQ ID NOs: 1 to 10; or
in a first terminal or a second terminal of the fully complementary polynucleotide sequence to any one of the SEQ ID NOs: 1 to 10.

3. The aptamer of the claim 1,
wherein the aptamer conjugates with an imaging agent selected from an inorganic sulfide, an oxide, a halide, a contrast medium and a fluorescent protein.

* * * * *